US007517957B2

(12) United States Patent
Chang et al.

(10) Patent No.: US 7,517,957 B2
(45) Date of Patent: Apr. 14, 2009

(54) HUMAN SLAP-2: A NOVEL SH2/ SH3 DOMAIN-CONTAINING HUMAN SLAP HOMOLOGUE HAVING IMMUNE CELL-SPECIFIC EXPRESSION

(75) Inventors: Han Chang, Princeton Junction, NJ (US); Wen-Pin Yang, Princeton, NJ (US); Yuli Wu, Newtown, PA (US); Gena S. Whitney, Lawrenceville, NJ (US); Juan J. Perez-villar, Mercerville, NJ (US); Steven B. Kanner, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 364 days.

(21) Appl. No.: 11/429,515

(22) Filed: May 5, 2006

(65) Prior Publication Data

US 2006/0193858 A1      Aug. 31, 2006

Related U.S. Application Data

(62) Division of application No. 09/988,971, filed on Nov. 20, 2001, now Pat. No. 7,101,686.

(60) Provisional application No. 60/252,545, filed on Nov. 22, 2000.

(51) Int. Cl.
C07K 14/00    (2006.01)
(52) U.S. Cl. .................................................... 530/350
(58) Field of Classification Search ........................ None
See application file for complete search history.

(56) References Cited

FOREIGN PATENT DOCUMENTS

| WO | WO9526983 | 10/1995 |
|----|-----------|---------|
| WO | WO 00/58473 | 10/2000 |
| WO | WO0216599 | 2/2002 |
| WO | WO0242452 | 5/2002 |
| WO | WO02055707 | 7/2002 |

OTHER PUBLICATIONS

Mikayama et al. PNAS, 1993. 90: 10056-10060.*
Burgess et al(J Cell Biol. 111:2129-2138, 1990.*
Wang et al. JBC, 2001 276:49213-49220.*
Whisstock et al. Quarterly Review of Biophysics, 2003, 36, pp. 307-340.*
Attwood (Science 2000; 290:471-473.*
Ngo et al, The Protein Folding Problem and Tertiary Structure Prediction, 1994. (ed.), Birkhauser, Boston, MA, pp. 433 and 492-495.*
NCBI Accession No. NP_115590, Loreto, et al., Dec. 22, 2003.
NCBI Accession No. AF326353, Holland, et al., Nov. 8, 2001.
NCBI Accession No. AF290985, Loreto, et al., Jan. 21, 2003.
NCBI Accession No. AF287467, Loreto, et al., Jun. 3, 2002.
NCBI Accession No. AAL86403, Pandey, et al., May 20, 2002.
NCBI Accession No. gi:17351918, Loreto, et al., Jun. 3, 2002.
NCBI Accession No. gi: 14149916, Loreto, et al., May 7, 2003.
Okano, et al. (1991) J. of Neurochemistry 56:560-567.
Stein, et al. (1988) Nucleic Acids Research 16(8):3209-3221.
Zhang, et al (1998) Cell Press 92:83-92.
Chan, et al. (1992) Cell Press 71:649-662.
Chan, et al. (1995) EMBO J. 14(11):2499-2508.
Pawson, et al. (1997) Science 278:2075-2080.
Pandey, et al. (1995) J. of Biological Chemistry 270(33):19201-19204.
Pandey, et al. (2002) J. of Biological Chemsitry 277(21)19131-19138.
Wardenburg, et al. (1996) J. of Biological Chemistry 271(33):19641-19644.
Kelly, et al. (2000) Current Opinion in Immunology 12:267-275.
Myung, et. al. (2000) Current Opinion in Immunology 12:256-266.
Tomlinson, et al. (2000) Review Immunology Today 21(11)584-591.
Tomohiro Kurosaki (1999) Annual Rev. Immunol. 17:555-592.
Holland, et al. (2001) J. Exp. Med. 194(9)1263-1276.
Sosinowski, et al. (2000) J. Exp. Med. 191(3)463-473.
Loreto, et al. (2002) Molecular and Cellular Biology 22(12):4241-4255.
Williams, et al. (1998) Molecular and Cellular Biology 18(3)1388-1399.
Tang, et al. (1999) Proc. Natl. Acad. Sci. 96:9775-9780.
Loreto, et al. (2003) Oncogene 22:266-273.
Pandey, et al. (2002) J. of Biological Chem. 277(21):19131-19138.
NCBI Accession No. gi:14149916, Loreto et al. May 7, 2003.
NCBI Accession No. gi:16797891, Holland et al. Nov. 8, 2001.
NCBI Accession No. gi:17351920, Loreto et al. Jan. 21, 2008.
NCBI Accession No. gi:27469842, R. Strausberg, Jan. 2, 2003.
NCBI Accession No. gi:17351918, Loreto et al. Jun. 3, 2002.
NCBI Accession No. gi:19224131, Pandey et al. May 20, 2002.
Peterson, et al. (1998) Current Opinion in Immunology 10:337:344.
Pandey, et al. (1995) J. of Biol. Chem. 270 (3):19201-19204.
Sosinowski, et al. (2000) J. Exp. Med. 191(3):463-473.

(Continued)

Primary Examiner—Michail A Belyavskyi
(74) Attorney, Agent, or Firm—Stephen C. D'Amico

(57) ABSTRACT

The present invention describes a newly discovered full-length polynucleotide encoding an SH2/SH3 domain-containing adapter protein, called hSLAP-2, cloned, isolated and identified. Also described are the hSLAP-2 polypeptide sequence, expression vectors, host cells, agonists, antagonists, anti-sense molecules, and antibodies related to the polynucleotide and/or polypeptide of the present invention. Methods for screening for modulators, particularly inhibitors, of the hSLAP-2 protein and use of the hSLAP-2 polynucleotide and polypeptide for therapeutics and diagnostics are described.

9 Claims, 8 Drawing Sheets

OTHER PUBLICATIONS

Holland et al., J. Exp. Med. 194(9):1263-1276 (2001).
NCBI Entrez Accession No. gi|14149916.
NCBI Entrez Accession No. gi|17351921
NCBI Entrez Accession No. gi|10438228.
NCBI Entrez Accession No. gi|14770662.
NCBI Entrez Accession No. gi|6983726.
NCBI Entrez Accession No. gi|17351923.
NCBI Entrez Accession No. AK025645.
Incyte Est ID No. 3182427.

* cited by examiner

FIG. 1

```
   1 CCCACGCGTCCGGTCGGAGCTAGAGCTCCAAGGACCCCACGCCTGTGTCTCTGTGACAGA
  61 GCTCAAAGGGCCCTGGGCCTTCCCTCCCTGGCTCGGCTGTGCTTGGGAGGGTTCCCCAGT
 121 CCAGAATCCCTAAGGAGCATGGGGCAGCTGATCCATCCCTGGTGTACAAACTGCTGACTG
 181 CAGACAGATGCTGAGCTACCCAAACCAACACCTAGCCTCTCCCTGAAGATCCTCCCAGGC
 241 TGAGAGAGTTCTGGGTGTCCTAGGACCAAGGACACTGGCAGACTTCCAGAAGGGCCCCCA
 301 AAGCCCTAACCTGTCCAGCCAGAGCATGCGTCTCAGCAGAGCTGTCTTCCCAAGCCTTTG
 361 ATGACAAACCAATTTCCCTCGATGATGTGCTTCTGAGTGCTCTGCTGAGGAACAATGGGA
 421 AGTCTGCCCAGCAGAAGAAAATCTCTGCCAAGCCCAAGCTTGAGTTCCTCTGTCCAAGGC
 481 CAGGGACCTGTGACCATGGAAGCAGAGAGAAGCAAGGCCACAGCCGTGGCCCTGGGCAGT
 541 TTCCCGGCAGGTGGCCCGGCCGAGCTGTCGCTGAGACTCGGGGAGCCATTGACCATCGTC
 601 TCTGAGGATGGAGACTGGTGGACGGTGCTGTCTGAAGTCTCAGGCAGAGAGTATAACATC
 661 CCCAGCGTCCACGTGGCCAAAGTCTCCCATGGGTGGCTGTATGAGGGCCTGAGCAGGGAG
 721 AAAGCAGAGGAACTGCTGTTGTTACCTGGGAACCCTGGAGGGGCCTTCCTCATCCGGGAG
 781 AGCCAGACCAGGAGAGGCTCTTACTCTCTGTCAGTCCGCCTCAGCCGCCCTGCATCCTGG
 841 GACCGGATCAGACACTACAGGATCCACTGCCTTGACAATGGCTGGCTGTACATCTCACCG
 901 CGCCTCACCTTCCCCTCACTCCAGGCCCTGGTGGACCATTACTCTGAGCTGGCGGATGAC
 961 ATCTGCTGCCTACTCAAGGAGCCCTGTGTCCTGCAGAGGGCTGGCCCGCTCCCTGGCAAG
1021 GATATACCCCTACCTGTGACTGTGCAGAGGACACCACTCAACTGGAAAGAGCTGGACAGC
1081 TCCCTCCTGTTTTCTGAAGCTGCCACAGGGGAGGAGTCTCTTCTCAGTGAGGGTCTCCGG
1141 GAGTCCCTCAGCTTCTACATCAGCCTGAATGACGAGGCTGTCTCTTTGGATGATGCCTAG
1201 GCCCAAAGGAGAGGCCAAAAGGGAAACCAAGGCTGCACACCTAGAACCCCAATTCAGCCT
1261 CCTGGGCACCCCAGAGGCAAGGCTGTGCACTCAGGGAGGGAGGGTGGGACACAGAGGTGC
1321 ATCTAGGGTCCCACCTGTACCCTTGCTCTTTCCTCTCTTAGCCCTTAGAAGTCACCTACT
1381 TCCTTCCAGTGCCATGATCCCACCTGCGACCTCTAGTGCGAGTGCAGAGAAGGTGGGACC
1441 AGGGCCAGGGTTCCAAAAAGAGAATAAGCCTCCTGGGGGGTCTGACCTAGTTAGTTCTTG
1501 AGTTTGGGGTTTCCAGTACCATCTGGATGCCCTGCCTGTTGAGCCCCATTCTACATCCCC
1561 ACCATTAACCAGGCCCCACCCACAAGGTAGAAACAACCCCTAGAGTCAACGAGAAAGTCA
1621 TTTTCAGAAAATCTACAAGTCTCGTTGAGACCACCACCATACCTCAGAAGGTAGGACTGT
1681 GGCCTAGAAGGGAAAGGAAAGCTGAGATGATGTCTTACCGTAGCAGCAGATCTTGGATGG
1741 TCCAGGCTCTATGTGACCTCCAGAGCAAAGAGAAAGACTTCGGACAGTCTAGGTCCTCAA
1801 ATGTCCCCATTGAGGACAACAGCCCCAGCTCTTTTTCTTTTTTTTTGAGACGGAGTCTT
1861 GCCCTGTTGCCCATGCTGGAGTGCAATGGCACGATCTCAGCTCACTGCAACCTCCATCTC
1921 CTGGATTCAAACAATTCTCCTGCCTCAGCCTCCAGAATAGCTGGGATTACAGGCGTACAC
1981 CACCATGCCTGGCTAATTTTTTGTATTTTTAGTAGACATGGGGTTTCACCACATTGGCC
2041 AGGCTGGTGTCGAACTCCTGACCTCAGGTGATCCACCCACCTTGGCCTCCCAAAGTGCTG
2101 GGATTACAGGTGTGAGCCACGGCACCCAGCCTAGCTCTCAGATCTCTATTTCATTTTGTG
2161 GCTTACCATTCCCTAGCACACTGGCCTTGCCATCTTGTGGCCGAATAAAAAATAACACCT
2221 CTTAAGTCTAGCACACTGCAGTGAGGCCAGGCACCTCAGTGCTGGGCAGGGCATCAGAA
2281 GGTGCTAAGCCCTCTCTCCACAATGCCAAGACGGAGACCACAGCCTACACCAAATCCAGC
2341 CCTTGATTTCCCTGCTGCCTCCATAAACAGAAAGAGGTCTGCTGGATCCGCTAAGGGATC
2401 AGGGAGAGGAAGAAAGAGGGATGGGGTGGGAGGCACCCCTCCAGTGCTCCTACTGGTTC
2461 CCAAGCTACAGGTGGGGTGGGAAAGGCTTTATCAGGTATCATCAACAGGTTCTCAATTAA
2521 AGATTTGATTTATTCAAGTATGTGAAAAAAAAAAAAAAAAAAAAA
```

```
   1 CCCACGCGTCCGGTCGGAGCTAGAGCTCCAAGGACCCCACGCCTGTGTCTCTGTGACAGA
  61 GCTCAAAGGGCCCTGGGCCTTCCCTCCCTGGCTCGGCTGTGCTTGGGAGGGTTCCCCAGT
 121 CCAGAATCCCTAAGGAGCATGGGGCAGCTGATCCATCCCTGGTGTACAAACTGCTGACTG
 181 CAGACAGATGCTGAGCTACCCAAACCAACACCTAGCCTCTCCCTGAAGATCCTCCCAGGC
 241 TGAGAGAGTTCTGGGTGTCCTAGGACCAAGGACACTGGCAGACTTCCAGAAGGGCCCCCA
 301 AAGCCCTAACCTGTCCAGCCAGAGCATGCGTCTCAGCAGAGCTGTCTTCCCAAGCCTTTG
 361 ATGACAAACCAATTTCCCTCGATGATGTGCTTCTGAGTGCTCTGCTGAGGAACAATGGGA
   1                                                             M  G

421 AGTCTGCCCAGCAGAAGAAAATCTCTGCCAAGCCCAAGCTTGAGTTCCTCTGTCCAAGGC
   3  S  L  P  S  R  R  K  S  L  P  S  P  S  L  S  S  S  V  Q  G

481 CAGGGACCTGTGACCATGGAAGCAGAGAGAAGCAAGGCCACAGCCGTGGCCCTGGGCAGT
  23  Q  G  P  V  T  M  E  A  E  R  S  K │A  T  A  V  A  L  G  S│

541 TTCCCGGCAGGTGGCCCGGCCGAGCTGTCGCTGAGACTCGGGGAGCCATTGACCATCGTC
  43 │F  P  A  G  G  P  A  E  L  S  L  R  L  G  E  P  L  T  I  V│

601 TCTGAGGATGGAGACTGGTGGACGGTGCTGTCTGAAGTCTCAGGCAGAGAGTATAACATC
  63 │S  E  D  G  D  W  W  T  V  L  S  E  V  S  G  R  E  Y  N  I│

661 CCCAGCGTCCACGTGGCCAAAGTCTCCCATGGGTGGCTGTATGAGGGCCTGAGCAGGGAG
  83 │P  S  V  H  V  A  K  V│S  H  G  W  L  Y  E  G  L  S  R  E

721 AAAGCAGAGGAACTGCTGTTGTTACCTGGGAACCCTGGAGGGGCCTTCCTCATCCGGGAG
 103  K  A  E  E  L  L  L  L  P  G  N  P  G  G  A  F  L  I  R  E

781 AGCCAGACCAGGAGAGGCTCTTACTCTCTGTCAGTCCGCCTCAGCCGCCCTGCATCCTGG
 123  S  Q  T  R  R  G  S  Y  S  L  S  V  R  L  S  R  P  A  S  W

841 GACCGGATCAGACACTACAGGATCCACTGCCTTGACAATGGCTGGCTGTACATCTCACCG
 143  D  R  I  R  H  Y  R  I  H  C  L  D  N  G  W  L  Y  I  S  P

901 CGCCTCACCTTCCCCTCACTCCAGGCCCTGGTGGACCATTACTCTGAGCTGGCGGATGAC
 163  R  L  T  F  P  S  L  Q  A  L  V  D  H  Y  S  E  L  A  D  D

961 ATCTGCTGCCTACTCAAGGAGCCCTGTGTCCTGCAGAGGGCTGGCCCGCTCCCTGGCAAG
 183  I  C  C  L  L  K  E  P  C  V  L  Q  R  A  G  P  L  P  G  K

1021 GATATACCCCTACCTGTGACTGTGCAGAGGACACCACTCAACTGGAAAGAGCTGGACAGC
 203  D  I  P  L  P  V  T  V  Q  R  T  P  L  N  W  K  E  L  D  S

1081 TCCCTCCTGTTTTCTGAAGCTGCCACAGGGGAGGAGTCTCTTCTCAGTGAGGGTCTCCGG
 223  S  L  L  F  S  E  A  A  T  G  E  E  S  L  L  S  E  G  L  R

1141 GAGTCCCTCAGCTTCTACATCAGCCTGAATGACGAGGCTGTCTCTTTGGATGATGCCTAG
 243  E  S  L  S  F  Y  I  S  L  N  D  E  A  V  S  L  D  D  A  *

1201 GCCCAAAGGAGAGGCCAAAAGGGAAACCAAGGCTGCACACCTAGAACCCCAATTCAGCCT
1261 CCTGGGCACCCCAGAGGCAAGGCTGTGCACTCAGGGAGGGAGGGTGGGACACAGAGGTGC
1321 ATCTAGGGTCCCACCTGTACCCTTGCTCTTTCCTCTCTTAGCCCTTAGAAGTCACCTACT
1381 TCCTTCCAGTGCCATGATCCCACCTGCGACCTCTAGTGCGAGTGCAGAGAAGGTGGGACC
1441 AGGGCCAGGGTTCCAAAAAGAGAATAAGCCTCCTGGGGGGTCTGACCTAGTTAGTTCTTG
1501 AGTTTGGGGTTTCCAGTACCATCTGGATGCCCTGCCTGTTGAGCCCCATTCTACATCCCC
1561 ACCATTAACCAGGCCCCACCCACAAGGTAGAAACAACCCCTAGAGTCAACGAGAAAGTCA
```

FIG. 3B

```
1621  TTTTCAGAAAATCTACAAGTCTCGTTGAGACCACCACCATACCTCAGAAGGTAGGACTGT
1681  GGCCTAGAAGGGAAAGGAAAGCTGAGATGATGTCTTACCGTAGCAGCAGATCTTGGATGG
1741  TCCAGGCTCTATGTGACCTCCAGAGCAAAGAGAAAGACTTCGGACAGTCTAGGTCCTCAA
1801  ATGTCCCCCATTGAGGACAACAGCCCCAGCTCTTTTTCTTTTTTTTGAGACGGAGTCTT
1861  GCCCTGTTGCCCATGCTGGAGTGCAATGGCACGATCTCAGCTCACTGCAACCTCCATCTC
1921  CTGGATTCAAACAATTCTCCTGCCTCAGCCTCCAGAATAGCTGGGATTACAGGCGTACAC
1981  CACCATGCCTGGCTAATTTTTTTGTATTTTTAGTAGACATGGGGTTTCACCACATTGGCC
2041  AGGCTGGTGTCGAACTCCTGACCTCAGGTGATCCACCCACCTTGGCCTCCCAAAGTGCTG
2101  GGATTACAGGTGTGAGCCACGGCACCCAGCCTAGCTCTCAGATCTCTATTTCATTTGTG
2161  GCTTACCATTCCCTAGCACACTGGCCTTGCCATCTTGTGGCCGAATAAAAAATAACACCT
2221  CTTAAGTCTAGCACACTGCAGTGAGGCCAGGCACCTCAGTGCTGGGCAGGGGCATCAGAA
2281  GGTGCTAAGCCCTCTCTCCACAATGCCAAGACGGAGACCACAGCCTACACCAAATCCAGC
2341  CCTTGATTTCCCTGCTGCCTCCATAAACAGAAAGAGGTCTGCTGGATCCGCTAAGGGATC
2401  AGGGAGAGGAAGAAAGAGGGATGGGGTGGGAGGCACCCCTCCAGTGCTCCTACTGGTTC
2461  CCAAGCTACAGGTGGGGTGGGAAAGGCTTTATCAGGTATCATCAACAGGTTCTCAATTAA
2521  AGATTTGATTTATTCAAGTATGTGAAAAAAAAAAAAAAAAAAAAAA
```

FIG. 4

| Homology | Amino acid level | |
|---|---|---|
| | Similarity | Identity |
| human SLAP x mouse SLAP | 89.9% | 88.0% |
| human SLAP x human SLAP-2 | 58.4% | 47.4% |
| mouse SLAP x human SLAP-2 | 70.0% | 58.1% |

FIG. 5

```
hSLAP-2    1  MGSLPSRRKSLPSPSLSSSVQGQGPVTMEAERSKATAVALGSFPAGGPAE
                 : .  || |.|.       : |.         |   :|.   .
hSLAP      1  ...MGNSMKSTPAPA.......ERPLPNPEGLDSDFLAVLSDYPSPDISP

51  LSLRLGEPLTIVSEDGDWWTVLSEVSGREYNIPSVHVAKVSHGWLYEGLS
              | || |  ::|::| ||  :|  .|||  || :  ||:| ||||:|||
          41  PIFRRGEKLRVISDEGGWWKAISLSTGRESYIPGICVARVYHGWLFEGLG

101  REKAEELLLLPGNPGGAFLIRESQTRRGSYSLSVRLSRPASWDRIRHYRI
              |:|||||| ||    |.|:||||:|::| ||||||      .::||||
          91  RDKAEELLQLPDTKVGSFMIRESETKKGFYSLSVR......HRQVKHYRI

151  HCLDNGWLYISPRLTFPSLQALVDHYSELADDICCLLKEPCVLQRAGPLP
              | | | ||||||||  |: ||.||||.||  :||.|   ||. |
         135  FRLPNNWYYISPRLTFQCLEDLVNHYSEVADGLCCVLTTPCLTQSTAAPA

201  GKDIPLPVTVQRTPLNWK...ELDSSLLFSEAATG.EESLLSEGLRESLS
              :    |||...  ..|:      |       .|   |  :|||  |||||:.
         185  VRASSSPVTLRQKTVDWRRVSRLQEDPEGTENPLGVDESLFSYGLRESIA

247  FYISLNDEAVSLDDA...........................
              |:||  |   .  |
         235  SYLSLTSEDNTSFDRKKKSISLMYGGSKRKSSFFSSPPYFED
```

FIG. 6

```
hSLAP   1 MGNSMKSTPAPAERPLPNPEGLDSDFLAVLSDYPSPDISPPIFRRGEKLR
          ||||||||  |.||||  .|||:|||||| .||||||||||||||||||
mSLAP   1 MGNSMKSTSPPSERPLSSSEGLESDFLAVLTDYPSPDISPPIFRRGEKLR

51 VISDEGGWWKAISLSTGRESYIPGICVARVYHGWLFEGLGRDKAEELLQL
          ||||||||||||||||||||||||||||||||||||||||||||||||||
       51 VISDEGGWWKAISLSTGRESYIPGICVARVYHGWLFEGLGRDKAEELLQL

101 ·PDTKVGSFMIRESETKKGFYSLSVRHRQVKHYRIFRLPNNWYYISPRLTF
          ||||:|||||||||||||||||||||||||||||||||||||||||||||
      101 PDTKIGSFMIRESETKKGFYSLSVRHRQVKHYRIFRLPNNWYYISPRLTF

151 QCLEDLVNHYSEVADGLCCVLTTPCLTQSTAAPAVRAS.....SSPVTLR
          ||||||| ||||||||||||||||| |.  ||    |      ||||||
      151 QCLEDLVTHYSEVADGLCCVLTTPCLAQNIPAPTSHPSPCTSPGSPVTLR

196 QKTVDWRRVSRLQEDPEGTENPLGVDESLFSYGLRESIASYLSLTSEDNT
          ||| ||:|||||||  || |||| |||||||||||||||||||||:|..
      201 QKTFDWKRVSRLQEGSEGAENPLRVDESLFSYGLRESIASYLSLTGDDSS

246 SFDRKKKSISLMYGGSKRKSSFFSSPPYFED 276
          ||||||||:||||  |||||||||||.|||||
      251 SFDRKKKSLSLMYTGSKRKSSFFSAPQYFED 281
```

FIG. 7

```
hSLAP-2  1  MG.SLPSRRKSLPS..PSLSSSVQGQGPVTMEAERSKATAVALGSFPAGG
            || |: |    | || | ||||    :|    :|   |   || |  :|.
mSLAP    1  MGNSMKS..TSPPSERP.LSSS...EG...LE...SDFLAV.LTDYPS..

48  PAELS...LRLGEPLTIVSEDGDWWTVLSEVS.GRE.YNIPSVHVAKVSH
            | ::|       | || | ::|::| ||   :| .| ||| | || : ||:| |
        36  P.DISPPIFRRGEKLRVISDEGGWWKAIS.LSTGRESY.IPGICVARVYH

93  GWLYEGLSREKAEELLLLPGNPGGAFLIRESQTRRGSYSLSVRLSRPASW
            |||:||| |:|||||| ||      |.|:||||:|::| |||||| |
        83  GWLFEGLGRDKAEELLQLPDTKIGSFMIRESETKKGFYSLSVR.HR....

143  DRIRHYRIHCLDNGWLYISPRLTFPSLQALVDHYSELADDICCLLKEPCV
            .::||||   | | | ||||||||  |: || ||||.|| :||.|    ||.
       128  .QVKHYRIFRLPNNWYYISPRLTFQCLEDLVTHYSEVADGLCCVLTTPCL

193  LQR..A.....GPL..PGKDIPLPVTV.QRTPLNWKELDSSLLFSEAATG
            |    |      |    ||     |||. |:|   .|| . || |    | .|
       177  AQNIPAPTSHPSPCTSPGS....PVTLRQKT.FDWKRV.SRL..QEGSEG

233  .E......ESLLSEGLRESLSFYISL.NDEAVSLD
            |         ||| | |||||:. |:|| |:. | |
       219  AENPLRVDESLFSYGLRESIASYLSLTGDDSSSFD
```

HUMAN SLAP-2: A NOVEL SH2/ SH3 DOMAIN-CONTAINING HUMAN SLAP HOMOLOGUE HAVING IMMUNE CELL-SPECIFIC EXPRESSION

This application is a divisional application of non-provisional application U.S. Ser. No. 09/988,971, filed Nov. 20, 2001, now U.S. Pat. No. 7,101,686, which claims benefit to provisional application U.S. Ser. No. 60/252,545, filed Nov. 22, 2000.

FIELD OF THE INVENTION

The invention relates to the identification and cloning of a novel full-length human SLAP-2 gene and its encoded polypeptide product, SLAP (Src-Like Adapter Protein), which contains an SH2 (Src homology 2) domain and an SH3 (Src homology 3) domain. By homology analysis, SLAP-2 is a member of the SLAP family of adapter proteins and is expressed primarily in immune cells. The invention further relates to the use of the novel SLAP-2 gene and its encoded product as targets for therapeutic intervention in immunological and inflammatory disorders, autoimmune diseases, pulmonary diseases, and cancer.

BACKGROUND OF THE INVENTION

Receptor signaling pathways and intracellular signaling by receptor tyrosine kinases are intimately involved in cell growth and differentiation. The binding of a particular growth factor or cellular ligand to its receptor on a cell's plasma membrane can stimulate a wide variety of biochemical responses, including changes in ion fluxes, activation of various kinases, alteration of cell shape, transcription of various genes and modulation of enzymatic activities in cellular metabolism.

Many cell receptors are tyrosine kinases whose signaling is dependent upon tyrosine phosphorylation of both the receptor and other molecules. Specific phosphorylated tyrosine residues on these receptors recruit soluble intracellular signaling molecules to the receptor-ligand complex upon extracellular ligand stimulation, thus initiating the intracellular signaling cascade that involves secondary signal transducer molecules generated by the activated receptor. The signal can then proceed through a series of steps to the nucleus and other subcellular locations where the final effects of activation by the extracellular ligand are produced. Recruitment of other molecules in the signaling pathway is often accomplished by adapter molecules, which contain only protein-protein interaction domains (e.g., SH2 and SH3 domains) and have no associated enzymatic activity. By isolating and characterizing the adapter proteins and the molecules that interact with these adapters, important components of the signaling mechanism can be discovered, monitored and controlled.

For example, one such adapter protein is Grb2, a 24-25 kDa cytosolic adapter protein containing two SH3 domains flanking an SH2 domain, which is known to be involved in linking many important molecules in receptor-ligand signal transduction (E. J. Lowenstein et al., 1992, *Cell*, 70:431-442 and J. Downward, 1994, *FEBS Letters*, 338:113-117). The central SH2 domain of Grb2 binds to an autophosphorylation site on the receptor and the two flanking SH3 domains link to intracellular effector target molecules. An example of one such target molecule is the mammalian homologue of the *Drosophila* 'son of sevenless' (SOS) protein, which is a guanine nucleotide exchange factor for ras; thus, Grb2 links receptors with the ras signal transduction pathway. It is now known that the SH3 domains also link to a number of other proteins involved in the signaling pathway, including Vav (R. Ren et al., 1994, *Genes Dev.*, 8:783-795; J. Wu et al., 1996, *Immunity*, 4:593; and L. Tuosto et al., 1996, *J. Exp. Med.*, 184:1161); c-abl (Z. S. Ye and D. Baltimore, 1994, *Proc. Natl. Acad. Sci., USA*, 91:12629-12633); dynamin (I. Gout et al., 1993, *Cell*, 75:25-36); and SLP-76 (J. K. Jackman et al., 1995, *J. Biol. Chem.*, 270:7029-7032). In addition, several other binding proteins have been noted during B- and T-cell signaling (see, e.g., K. Reif et al., 1994, *J. Biol. Chem.*, 269:14081-14087 and D. G. Motto et al., 1994, *J. Biol. Chem.*, 269:21608-21613).

The SLP-76 family of adapter protein molecules includes the SLP-76, BLNK and Clnk proteins (P. S. Myung et al., 2000, "Adapter proteins in lymphocyte antigen-receptor signaling", *Curr. Opin. Immunol.*, 12:256-266 and M. Y. Cao et al., 1999, "Clnk, a novel SLP-76-related adapter molecule expressed in cytokine-stimulated hemopoietic cells", *J. Exp. Med.*, 190:1527-1534). Expressed exclusively in cells of hematopoietic origin, these adapter proteins are involved in intracellular signal transduction. SLP-76 is an SH2/SH3 domain-containing 76 kDa leukocyte protein that undergoes tyrosine phosphorylation following activation of the T-cell antigen receptor (TCR). SLP-76, upon tyrosine phosphorylation, interacts with Grb2 and phospholipase C-γ (PLC-γ), (J. K. Jackman et al., supra). The phosphorylation of SLP-76 on tyrosine is required for TCR-mediated cytokine secretion.

SH2 domain-containing proteins bind phosphorylated tyrosine residues and transmit important intracellular signals in many cell types. In the immune system, SH2 domain-containing proteins, such as SLP-76 and BLNK, play crucial roles in T-cell and B-cell activation. Therefore, SH2 domain-containing proteins are likely to be important targets for therapeutic intervention in immunological disorders, including autoimmune disorders and inflammatory indications.

With particular regard to B-cells, cell function is dependent on the ability of the membrane B-cell receptor (BCR) to bind to antigen and induce an efficient cascade of intracellular biochemical signaling events from the membrane to the nucleus. These events culminate in the cytosol to rearrange the morphology of the cell through cytoskeletal reorganization and in the nucleus to activate the transcription of new genes to promote cellular proliferation and differentiation. Such biochemical and cellular mechanisms are required for B-cells to mature and function to produce an efficient immune response to foreign pathogens. Conversely, the abnormal activation of B-cells can lead to unregulated cellular proliferation and uncontrolled clonal expansion, resulting in B-cell tumors, lymphomas and leukemias. In addition, unregulated activation of B-cells may also contribute to a variety of autoimmune diseases mediated by self-reactive antibodies.

In the case of T-cells, unregulated activation of the TCR can lead to aberrant T-cell growth, resulting in, for example, T-cell tumors, lymphomas, leukemias and thymomas. Thus, the ability to modulate TCR- and BCR-mediated signaling events may provide a rational approach to the treatment of T- and B-cell mediated tumors, and the like, as well as provide therapies for autoimmune diseases in which aberrant B-cell activation may be the culprit for cell destruction by autoreactive antibodies.

Because aberrant or uncontrolled regulation of the cellular processes involved in cell growth can have disastrous effects, it is important to elucidate and gain control over these processes. This requires identifying molecules that participate in the signaling events that lead to mitogenesis and dissecting their functions and mechanisms of action. The identification of these participants is important for a wide range of diagnostic, therapeutic and screening applications. More specifically, by understanding the structure of a particular participant in a receptor ligand activation cascade, one can rationally design compounds that affect that cascade, to either activate an otherwise inactive pathway, or inactivate an overly active pathway.

Similarly, having identified a particular molecule in a ligand receptor cascade, situations in which that cascade is defective can also be identified and intervention can be achieved by means of therapeutic compounds or drugs, to prevent the development of a particular pathological state. The identification of participants in particular receptor ligand activation cascades and intracellular signaling events is thus of critical importance for screening compounds that affect these cascades and events, and for treating a variety of disorders resulting from anomalies in these cascades and events as therapeutic agents. The present invention meets these and several additional needs.

Also, the discovery of human SLAP-2, a new member of the SLAP family of adapter proteins, and the polynucleotide encoding this protein, provides the art with new compositions and methods of use and treatment for the diagnosis, screening, monitoring, therapy, and prevention of immune system related conditions or diseases, particularly those involving T-cell and B-cell neoplasms; inflammation disorders, diseases and conditions, rheumatoid arthritis, osteoarthritis, psoriasis, rhinitis, inflammatory bowel disease (Crohn's and ulcerative colitis), allergies, particularly those involving hyperactivity of B-cells and T-cells, or other immune cells, such as mast cells or eosinophils; autoimmune diseases such as systemic lupus erythematosus and multiple sclerosis; pulmonary diseases including asthma, acute respiratory distress syndrome, and chronic obstructive pulmonary disorder; tissue/organ rejection; and cancer.

SUMMARY OF THE INVENTION

The present invention provides a newly discovered full-length human SH2-/SH3-domain containing gene and its encoded product, called hSLAP-2 (Human Src-Like Adapter Protein-2), which has homology to hSLAP (hSLAP) and mSLAP (mouse SLAP).

It is an object of the present invention to provide an isolated full-length hSLAP-2 polynucleotide as depicted in SEQ ID NO:1. The present invention also provides a polynucleotide sequence comprising the complement of SEQ ID NO:1, or variants thereof. In addition, the present invention features polynucleotide sequences which hybridize under moderate or high stringency conditions to the polynucleotide sequence of SEQ ID NO:1.

It is another object of the present invention to provide the human hSLAP-2 polypeptide, encoded by the polynucleotide of SEQ ID NO:1 and having the amino acid sequence of SEQ ID NO:2, or a functional or biologically active portion thereof. In accordance with the present invention, an isolated, substantially purified full-length human SLAP-2 protein is provided.

It is a further object of the present invention to provide compositions comprising the human SLAP-2 polynucleotide sequence, or a fragment thereof, or the encoded hSLAP-2 polypeptide, or a fragment or portion thereof. Also provided by the present invention are pharmaceutical compositions comprising at least one hSLAP-2 polypeptide, or a functional portion thereof, wherein the compositions further comprise a pharmaceutically acceptable carrier, excipient, or diluent.

It is a further object of the invention to provide an antisense of the human SLAP-2 nucleic acid sequence, as well as oligonucleotides, fragments, or portions of the hSLAP-2 nucleic acid molecule or anti-sense molecule. Also provided are expression vectors and host cells comprising polynucleotides that encode the human SLAP-2 polypeptide, or portions or fragments thereof.

It is an object of the present invention to provide methods for producing a polypeptide comprising the amino acid sequence depicted in SEQ ID NO:2, or a fragment thereof, comprising the steps of a) cultivating a host cell containing an expression vector containing at least a functional fragment of the polynucleotide sequence encoding the human SLAP-2 polypeptide according to this invention under conditions suitable for the expression of the polynucleotide; and b) recovering the polypeptide from the host cell.

It is a further object of the present invention to provide antibodies, and binding fragments thereof, which bind specifically to the hSLAP-2 polypeptide, or an epitope thereof, for use as therapeutics and diagnostic agents.

It is an object of the present invention to provide methods for screening for agents or molecules which bind to and/or modulate human SLAP-2 polypeptide, e.g., inhibitors, other intracellular signaling molecules and antagonists, as well as the modulators, particularly, inhibitors and antagonists, particularly those that are obtained from the screening methods described. Also provided are methods to screen for inhibitors of the interaction, e.g., a binding interaction, of the hSLAP-2 protein with other signaling proteins, particularly those having SH2 and SH3 interaction domains.

It is also an object of the present invention to provide a substantially purified antagonist or inhibitor of the polypeptide of SEQ ID NO:2. In this regard, and by way of example, a purified antibody that binds to a polypeptide comprising the amino acid sequence of SEQ ID NO:2 is provided.

It is a further object of the present invention to provide hSLAP-2 nucleic acid sequences, polypeptide, peptides and antibodies for use in the diagnosis and/or screening of disorders or diseases associated with expression of the polynucleotide and its encoded polypeptide as described herein.

It is an object of the present invention to provide kits for screening and diagnosis of disorders associated with aberrant or uncontrolled cellular development and with the expression of the hSLAP-2 polynucleotide and its encoded polypeptide as described herein.

It is an object of the present invention to further provide methods for the treatment or prevention of immune cell disorders or diseases, e.g., B- or T-cell tumors, lymphomas, leukemias, autoimmune diseases, or inflammation, involving administering to an individual in need of treatment or prevention an effective amount of a purified antagonist or agonist of the hSLAP-2 polypeptide. It is an object of the present invention to provide a method for detecting a polynucleotide that encodes the hSLAP-2 polypeptide in a biological sample comprising the steps of: a) hybridizing the complement of the polynucleotide sequence encoding SEQ ID NO:2 to a nucleic acid material of a biological sample, thereby forming a hybridization complex; and b) detecting the hybridization complex, wherein the presence of the complex correlates with the presence of a polynucleotide encoding the hSLAP-2 polypeptide in the biological sample. The nucleic acid material may be further amplified by the polymerase chain reaction prior to hybridization.

Further objects, features and advantages of the present invention will be better understood upon a reading of the detailed description of the invention when considered in connection with the accompanying figures/drawings.

BRIEF DESCRIPTION OF THE FIGURES

FIG. 1 shows the full-length polynucleotide sequence of human SLAP-2 cDNA of the present invention (SEQ ID NO:1; clone 13).

FIG. 2 shows the amino acid sequence comprising the hSLAP-2 polypeptide (SEQ ID NO:2).

FIGS. 3A-3B show the nucleic acid sequence of human SLAP-2 cDNA (SEQ ID NO:1), and the deduced, encoded amino acid sequence of the human SLAP-2 gene product (SEQ ID NO:2). The SH3 domain is boxed. The SH2 domain is underlined. Putative tyrosine phosphorylation sites are in boldface type.

FIG. 4 shows the homology between human SLAP (hSLAP), murine SLAP (mSLAP), and human SLAP-2 (hSLAP-2). Results are shown in both percentages of similarity and identity at the amino acid level.

FIG. 5 presents an alignment of hSLAP-2 (SEQ ID NO:2) and hSLAP (SEQ ID NO:6) amino acid sequences. Lines between resides indicate identity, double dots indicate conservative differences, and single dots indicate non-conservative differences. Individual dots above the residues demarcate every $10^{th}$ amino acid.

FIG. 6 shows the alignment of hSLAP (SEQ ID NO:6) and mSLAP (SEQ ID NO:7) amino acid sequences. Lines between residues indicate identity, double dots indicate conservative differences, and single dots indicate non-conservative differences. Individual dots above the residues demarcate every $10^{th}$ amino acid.

FIG. 7 shows the alignment of hSLAP-2 (SEQ ID NO:2) and mSLAP (SEQ ID NO:7) amino acid sequences. Lines between residues indicate identity, double dots indicate conservative differences, and single dots indicate non-conservative differences. Individual dots above the residues demarcate every $10^{th}$ amino acid.

DETAILED DESCRIPTION OF THE INVENTION

Figure 8:
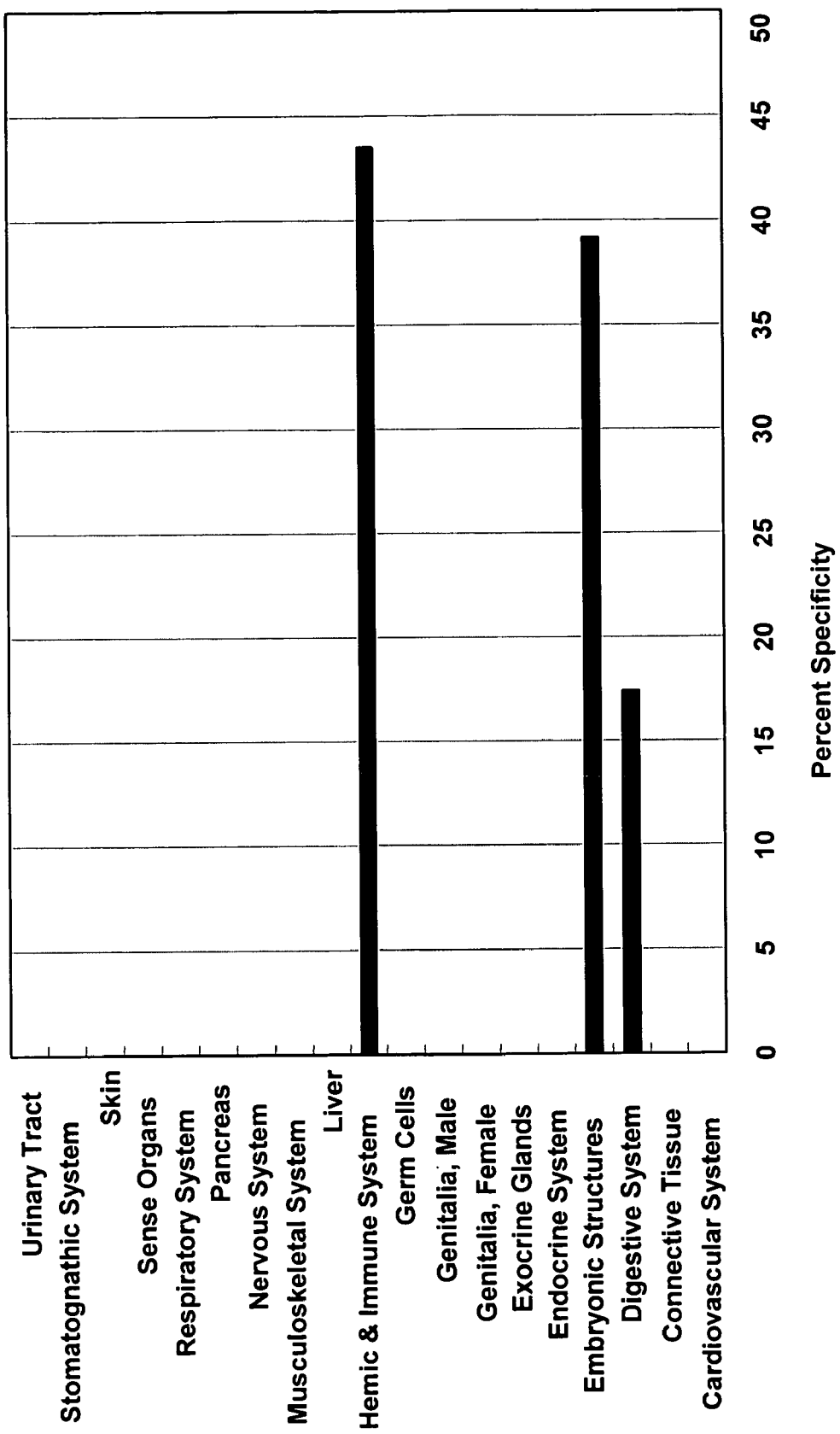
FIG. 8 depicts an electronic Northern analysis of the tissue expression of hSLAP-2.

The present invention provides a novel isolated polynucleotide (SEQ ID NO:1) encoding the full-length hSLAP-2 polypeptide (SEQ ID NO:2), a protein having similarity at the amino acid level to other SH2/SH3-domain containing adapter proteins which function in the receptor-ligand signal transduction pathway in cells of the hematopoietic lineage.

The following definitions are provided to more fully describe the present invention in its various aspects. The definitions are intended to be useful for guidance and elucidation, and are not intended to limit the disclosed invention and its embodiments.

Definitions

The "hSLAP-2 polypeptide" (or protein) refers to the amino acid sequence of substantially purified hSLAP-2, which, although isolated from a human cDNA library source according to the present invention, may be obtained from any species, preferably mammalian, including mouse, rat, non-human primates, and more preferably, human; and from a variety of sources, including natural, synthetic, semi-synthetic, or recombinant. Functional fragments of the hSLAP-2 polypeptide are also embraced by the present invention.

An "agonist" refers to a molecule which, when bound to the hSLAP-2 polypeptide, or a functional fragment thereof, increases or prolongs the duration of the effect of the hSLAP-2 polypeptide. Agonists may include proteins, nucleic acids, carbohydrates, or any other molecules that bind to and modulate the effect of hSLAP-2 polypeptide. An "antagonist" (e.g., inhibitor) refers to a molecule which, when bound to the hSLAP-2 polypeptide, or a functional fragment thereof, decreases or eliminates the amount or duration of the biological or immunological activity of hSLAP-2 polypeptide. Antagonists may include proteins, nucleic acids, carbohydrates, antibodies, or any other molecules that decrease, reduce or eliminate the effect of the hSLAP-2 polypeptide.

"Nucleic acid sequence", as used herein, refers to an oligonucleotide, nucleotide, or polynucleotide, and fragments or portions thereof, and to DNA or RNA of genomic or synthetic origin which may be single- or double-stranded, and represent the sense or anti-sense strand. By way of nonlimiting example, fragments include nucleic acid sequences that are greater than 20-60 nucleotides in length, and preferably include fragments that are at least 70-100 nucleotides, or which are at least 1000 nucleotides or greater in length. Nucleic acids for use as probes or primers may differ in length as described herein.

Similarly, "amino acid sequence" as used herein refers to an oligopeptide, peptide, polypeptide, or protein sequence, and fragments or portions thereof, and to naturally occurring or synthetic molecules. Amino acid sequence fragments are typically from about 4 or 5 to about 35, preferably from about 5 to about 15 or 20 amino acids in length and, optimally, retain the biological activity or function of the hSLAP-2 polypeptide.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule. In addition, the terms "hSLAP-2 polypeptide" and "hSLAP-2 protein" are frequently used interchangeably herein to refer to the encoded product of the hSLAP-2 nucleic acid sequence of the present invention.

A "variant" of the hSLAP-2 polypeptide can refer to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Minor variations may also include amino acid deletions or insertions, or both. Guidance in determining which amino acid residues may be substituted, inserted, or deleted without abolishing functional biological or immunological activity may be found using computer programs well known in the art, for example, DNASTAR software.

An "allele" or "allelic sequence" is an alternative form of the hSLAP-2 nucleic acid sequence. Alleles may result from at least one mutation in the nucleic acid sequence and may yield altered mRNAs or polypeptides whose structure or function may or may not be altered. Any given gene, whether natural or recombinant, may have none, one, or many allelic forms. Common mutational changes, which give rise to alleles, are generally ascribed to natural deletions, additions, or substitutions of nucleotides. Each of these types of changes may occur alone, or in combination with the others, one or more times in a given sequence.

Altered nucleic acid sequences encoding the hSLAP-2 polypeptide include nucleic acid sequences containing deletions, insertions and/or substitutions of different nucleotides resulting in a polynucleotide that encodes the same or a functionally equivalent hSLAP-2 polypeptide. Altered nucleic acid sequences may further include polymorphisms of the polynucleotide encoding the hSLAP-2 polypeptide; such polymorphisms may or may not be readily detectable using a particular oligonucleotide probe. The encoded protein may also contain deletions, insertions, or substitutions of amino acid residues, which produce a silent change and result in a functionally equivalent hSLAP-2 protein of the present invention. Deliberate amino acid substitutions may be made on the basis of similarity in polarity, charge, solubility, hydrophobicity, hydrophilicity, and/or the amphipathic nature of the residues, as long as the biological activity or function of hSLAP-2 protein is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; and phenylalanine and tyrosine.

"Peptide nucleic acid" (PNA) refers to an antisense molecule or anti-gene agent which comprises an oligonucleotide ("oligo") linked via an amide bond, similar to the peptide backbone of amino acid residues. PNAs typically comprise oligos of at least 5 nucleotides linked via amide bonds. PNAs may or may not terminate in positively charged amino acid residues to enhance binding affinities to DNA. Such amino acids include, for example, lysine and arginine, among others. These small molecules stop transcript elongation by binding to their complementary strand of nucleic acid (P. E. Nielsen et al., 1993, *Anticancer Drug Des.*, 8:53-63). PNA may be pegylated to extend their lifespan in the cell where they preferentially bind to complementary single stranded DNA and RNA.

"Oligonucleotides" or "oligomers" refer to a nucleic acid sequence, preferably comprising contiguous nucleotides, of at least about 6 nucleotides to about 60 nucleotides, preferably at least about 8 to 10 nucleotides in length, more preferably at least about 12 nucleotides in length, e.g., about 15 to 35 nucleotides, or about 15 to 25 nucleotides, or about 20 to 35 nucleotides, which can be typically used, for example, as probes or primers, in PCR amplification assays, hybridization assays, or in microarrays. It will be understood that the term oligonucleotide is substantially equivalent to the terms primer, probe, or amplimer, as commonly defined in the art. It will also be appreciated by those skilled in the pertinent art that a longer oligonucleotide probe, or mixtures of probes, e.g., degenerate probes, can be used to detect longer, or more complex, nucleic acid sequences, for example, genomic DNA. In such cases, the probe may comprise at least 20-200 nucleotides, preferably, at least 30-100 nucleotides, and more preferably, 50-100 nucleotides.

"Amplification" refers to the production of additional copies of a nucleic acid sequence and is generally carried out using polymerase chain reaction (PCR) technologies, which are well known and practiced in the art (see, D. W. Dieffenbach and G. S. Dveksler, 1995, *PCR Primer, a Laboratory Manual*, Cold Spring Harbor Press, Plainview, N.Y.).

"Microarray" is an array of distinct polynucleotides or oligonucleotides synthesized on a substrate, such as paper, nylon, or other type of membrane; filter; chip; glass slide; or any other type of suitable solid support.

The term "antisense" refers to nucleotide sequences, and compositions containing nucleic acid sequences, which are complementary to a specific DNA or RNA sequence. The term "antisense strand" is used in reference to a nucleic acid strand that is complementary to the "sense" strand. Antisense (i.e., complementary) nucleic acid molecules include PNA and may be produced by any method, including synthesis or transcription. Once introduced into a cell, the complementary nucleotides combine with natural sequences produced by the cell to form duplexes, which block either transcription or translation. The designation "negative" is sometimes used in reference to the antisense strand, and "positive" is sometimes used in reference to the sense strand.

The term "consensus" refers to the sequence that reflects the most common choice of base or amino acid at each position among a series of related DNA, RNA or protein sequences. Areas of particularly good agreement often represent conserved functional domains.

A "deletion" refers to a change in either nucleotide or amino acid sequence and results in the absence of one or more nucleotides or amino acid residues. By contrast, an insertion (also termed "addition") refers to a change in a nucleotide or amino acid sequence that results in the addition of one or more nucleotides or amino acid residues, as compared with the naturally occurring molecule. A "substitution" refers to the replacement of one or more nucleotides or amino acids by different nucleotides or amino acids.

A "derivative nucleic acid molecule" refers to the chemical modification of a nucleic acid encoding, or complementary to, the encoded hSLAP-2 polypeptide. Such modifications include, for example, replacement of hydrogen by an alkyl, acyl, or amino group. A nucleic acid derivative encodes a polypeptide, which retains the essential biological and/or functional characteristics of the natural molecule. A derivative polypeptide is one which is modified by glycosylation, pegylation, or any similar process that retains the biological and/or functional or immunological activity of the polypeptide from which it is derived.

The term "biologically active", i.e., functional, refers to a protein or polypeptide or peptide fragment thereof having structural, regulatory, or biochemical functions of a naturally occurring molecule. Likewise, "immunologically active" refers to the capability of the natural, recombinant, or synthetic hSLAP-2, or any oligopeptide thereof, to induce a specific immune response in appropriate animals or cells, for example, to generate antibodies, and to bind with specific antibodies.

The term "hybridization" refers to any process by which a strand of nucleic acid binds with a complementary strand through base pairing.

The term "hybridization complex" refers to a complex formed between two nucleic acid sequences by virtue of the formation of hydrogen bonds between complementary G and C bases and between complementary A and T bases. The hydrogen bonds may be further stabilized by base stacking interactions. The two complementary nucleic acid sequences hydrogen bond in an anti-parallel configuration. A hybridization complex may be formed in solution (e.g., $C_o t$ or $R_o t$ analysis), or between one nucleic acid sequence present in solution and another nucleic acid sequence immobilized on a solid support (e.g., membranes, filters, chips, pins, or glass slides, or any other appropriate substrate to which cells or their nucleic acids have been affixed).

The terms "stringency" or "stringent conditions" refer to the conditions for hybridization as defined by nucleic acid composition, salt and temperature. These conditions are well known in the art and may be altered to identify and/or detect identical or related polynucleotide sequences in a sample. A variety of equivalent conditions comprising either low, moderate, or high stringency depend on factors such as the length and nature of the sequence (DNA, RNA, base composition), reaction milieu (in solution or immobilized on a solid substrate), nature of the target nucleic acid (DNA, RNA, base composition), concentration of salts and the presence or absence of other reaction components (e.g., formamide, dextran sulfate and/or polyethylene glycol) and reaction temperature (within a range of from about 5° C. below the melting temperature of the probe to about 20° C. to 25° C. below the melting temperature). One or more factors may be varied to generate conditions, either low or high stringency, that is different from but equivalent to the aforementioned conditions.

As will be understood by those of skill in the art, the stringency of hybridization may be altered in order to identify or detect identical or related polynucleotide sequences. As will be further appreciated by the skilled practitioner, the melting temperature, Tm, can be approximated by the formulas as known in the art, depending on a number of parameters, such as the length of the hybrid or probe in number of nucleotides, or hybridization buffer ingredients and conditions (see, for example, T. Maniatis et al., *Molecular Cloning: A Laboratory Manual*, Cold Spring Harbor Laboratory, Cold Spring Harbor, N.Y., 1982 and J. Sambrook et al., *Molecular Cloning: A Laboratory Manual*, Cold Spring Harbor Laboratory, Cold Spring Harbor, N.Y., 1989; *Current Protocols in Molecular Biology*, Eds. F. M. Ausubel et al., Vol. 1, "Preparation and Analysis of DNA", John Wiley and Sons, Inc., 1994-1995, Suppls. 26, 29, 35 and 42; pp. 2.10.7-2.10.16; G. M. Wahl and S. L. Berger (1987; *Methods Enzymol.* 152:399-407); and A. R. Kimmel, 1987; *Methods of Enzymol.* 152: 507-511). As a general guide, Tm decreases approximately 1° C.-1.5° C. with every 1% decrease in sequence homology. Also, in general, the stability of a hybrid is a function of sodium ion concentration and temperature. Typically, the hybridization reaction is initially performed under conditions of low stringency, followed by washes of varying, but higher stringency. Reference to hybridization stringency, e.g., high, moderate, or low stringency, typically relates to such washing conditions.

Thus, by way of non-limiting example, "high stringency" refers to conditions that permit hybridization of those nucleic acid sequences that form stable hybrids in 0.018 M NaCl at about 65° C. (i.e., if a hybrid is not stable in 0.018 M NaCl at about 65° C., it will not be stable under high stringency conditions). High stringency conditions can be provided, for instance, by hybridization in 50% formamide, 5× Denhardt's solution, 5×SSPE (saline sodium phosphate EDTA) (1×SSPE buffer comprises 0.15 M NaCl, 10 mM $Na_2HPO_4$, 1 mM EDTA), (or 1×SSC buffer containing 150 mM NaCl, 15 mM $Na_3$ citrate•$2H_2O$, pH 7.0), 0.2% SDS at about 42° C., followed by washing in 1×SSPE (or saline sodium citrate, SSC) and 0.1% SDS at a temperature of at least about 42° C., preferably about 55° C., more preferably about 65° C.

"Moderate stringency" refers, by nonlimiting example, to conditions that permit hybridization in 50% formamide, 5× Denhardt's solution, 5×SSPE (or SSC), 0.2% SDS at 42° C. (to about 50° C.), followed by washing in 0.2×SSPE (or SSC) and 0.2% SDS at a temperature of at least about 42° C., preferably about 55° C., more preferably about 65° C.

"Low stringency" refers, by non-limiting example, to conditions that permit hybridization in 10% formamide, 5× Denhardt's solution, 6×SSPE (or SSC), 0.2% SDS at 42° C., followed by washing in 1×SSPE (or SSC) and 0.2% SDS at a temperature of about 45° C., preferably about 50° C.

For additional stringency conditions, see T. Maniatis et al., *Molecular Cloning: A Laboratory Manual*, Cold Spring Harbor Laboratory, Cold Spring Harbor, N.Y. (1982). It is to be understood that the low, moderate and high stringency hybridization/washing conditions may be varied using a variety of ingredients, buffers and temperatures well known to and practiced by the skilled practitioner.

The terms "complementary" or "complementarity" refer to the natural binding of polynucleotides under permissive salt and temperature conditions by base pairing. For example, the sequence "A-G-T" binds to the complementary sequence "T-C-A". Complementarity between two single-stranded molecules may be "partial", in which only some of the nucleic acids bind, or it may be complete when total complementarity exists between single-stranded molecules. The degree of complementarity between nucleic acid strands has significant effects on the efficiency and strength of hybridization between nucleic acid strands. This is of particular importance in amplification reactions, which depend upon binding between nucleic acids strands, as well as in the design and use of PNA molecules.

The term "homology" refers to a degree of complementarity. There may be partial sequence homology or complete homology, wherein "complete homology" is equivalent to identity, e.g., 100% identity. A partially complementary sequence that at least partially inhibits an identical sequence from hybridizing to a target nucleic acid is referred to using the functional term "substantially homologous". The inhibition of hybridization of the completely complementary sequence to the target sequence may be examined using a hybridization assay (e.g., Southern or Northern blot, solution hybridization, and the like) under conditions of low stringency. A substantially homologous sequence or probe will compete for and inhibit the binding (i.e., the hybridization) of a completely homologous sequence or probe to the target sequence under conditions of low stringency. Nonetheless, conditions of low stringency do not permit non-specific binding; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Those having skill in the art will know how to determine percent identity between/among sequences using, for example, algorithms such as those based on the CLUSTALW computer program (J. D. Thompson et al., 1994, *Nucleic Acids Research*, 2(22):4673-4680), or FASTDB, (Brutlag et al., 1990, *Comp. App. Biosci.*, 6:237-245), as known in the art. Although the FASTDB algorithm typically does not consider internal non-matching deletions or additions in sequences, i.e., gaps, in its calculation, this can be corrected manually to avoid an overestimation of the % identity. CLUSTALW, however, does take sequence gaps into account in its identity calculations.

A "composition comprising a given polynucleotide sequence" refers broadly to any composition containing the given polynucleotide sequence. The composition may comprise a dry formulation or an aqueous solution. Compositions comprising the polynucleotide sequence (SEQ ID NO:1) encoding hSLAP-2 polypeptide (SEQ ID NO:2), or fragments thereof, may be employed as hybridization probes. The probes may be stored in freeze-dried form and may be in association with a stabilizing agent such as a carbohydrate. In hybridizations, the probe may be employed in an aqueous solution containing salts (e.g., NaCl), detergents or surfactants (e.g., SDS), and other components (e.g., Denhardt's solution, dry milk, salmon sperm DNA, and the like).

The term "substantially purified" refers to nucleic acid sequences or amino acid sequences that are removed from their natural environment, i.e., isolated or separated by a variety of means, and are at least 60% free, preferably 75% to 85% free, and most preferably 90% or greater free from other components with which they are naturally associated.

The term "sample", or "biological sample", is meant to be interpreted in its broadest sense. A biological sample suspected of containing nucleic acid encoding the hSLAP-2 protein, or fragments thereof, or the hSLAP-2 protein itself, may comprise a body fluid, an extract from cells or tissue, chromosomes isolated from a cell (e.g., a spread of metaphase chromosomes), organelle, or membrane isolated from a cell, a cell, nucleic acid such as genomic DNA (in solution or bound to a solid support such as for Southern analysis), RNA (in solution or bound to a solid support such as for Northern analysis), cDNA (in solution or bound to a solid support), a tissue, a tissue print and the like.

"Transformation" refers to a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and partial bombardment. Such "transformed" cells include stably transformed cells in which the inserted DNA is capable of replication either as an autonomously replicating plasmid or as part of the host chromosome. Transformed cells also include those cells which transiently express the inserted DNA or RNA for limited periods of time.

The term "mimetic" refers to a molecule, the structure of which is developed from knowledge of the structure of the hSLAP-2 protein, or portions thereof, and as such, is able to affect some or all of the actions of the hSLAP-2 protein.

The term "portion" with regard to a protein (as in "a portion of a given protein") refers to fragments or segments, for example, peptides, of that protein. The fragments may range in size from four or five amino acid residues to the entire amino acid sequence minus one amino acid. Thus, a protein "comprising at least a portion of the amino acid sequence of SEQ ID NO: 2" encompasses the full-length human hSLAP-2 polypeptide, and fragments thereof.

The term "antibody" refers to intact molecules as well as fragments thereof, such as Fab, F(ab')$_2$, Fv, which are capable of binding an epitopic or antigenic determinant. Antibodies that bind to hSLAP-2 polypeptides can be prepared using intact polypeptides or fragments containing small peptides of interest or prepared recombinantly for use as the immunizing antigen. The polypeptide or oligopeptide used to immunize an animal can be derived from the transition of RNA or synthesized chemically, and can be conjugated to a carrier protein, if desired. Commonly used carriers that are chemically coupled to peptides include bovine serum albumin (BSA), keyhole limpet hemocyanin (KLH), and thyroglobulin. The coupled peptide is then used to immunize the animal (e.g, a mouse, a rat, or a rabbit).

The term "humanized" antibody refers to antibody molecules in which amino acids have been replaced in the non-antigen binding regions in order to more closely resemble a human antibody, while still retaining the original binding capability, e.g., as described in U.S. Pat. No. 5,585,089 to C. L. Queen et al.

The term "antigenic determinant" refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding" refer to the interaction between a protein or peptide and a binding molecule, such as an agonist, an antagonist, or an antibody. The interaction is dependent upon the presence of a particular structure (e.g., an antigenic determinant or epitope, or a structural determinant) of the protein that is recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody. In addition, the hSLAP-2 protein of the present invention contains an SH2/SH3 domain that serves as an interacting region of hSLAP-2 with other cellular proteins, putative tyrosine residues that may become phosphorylated and could bind to SH2 domains on other cellular proteins and an SH3 binding motif that may serve as a binding domain for other cellular proteins having an SH3 domain. (FIGS. 3A-3B).

The term "correlates with expression of a polynucleotide" indicates that the detection of the presence of ribonucleic acid that is similar to SEQ ID NO:1 by Northern analysis is indicative of the presence of mRNA encoding the hSLAP-2 polypeptide in a sample and thereby correlates with expression of the transcript from the polynucleotide encoding the protein.

An "alteration in the polynucleotide of SEQ ID NO:1" comprises any alteration in the sequence of the polynucleotides encoding the hSLAP-2 polypeptide, including deletions, insertions, and point mutations that may be detected using hybridization assays. Included within this definition is the detection of alterations to the genomic DNA sequence which encodes the hSLAP-2 polypeptide (e.g., by alterations in the pattern of restriction fragment length polymorphisms capable of hybridizing to SEQ ID NO:1), the inability of a selected fragment of SEQ ID NO:1 to hybridize to a sample of genomic DNA (e.g., using allele-specific oligonucleotide probes), and improper or unexpected hybridization, such as hybridization to a locus other than the normal chromosomal locus for the polynucleotide sequence encoding the hSLAP-2 polypeptide (e.g., using fluorescent in situ hybridization (FISH) to metaphase chromosome spreads).

DESCRIPTION OF THE PRESENT INVENTION

The present invention is based on the discovery of a novel full-length human Src homology 2-/Src homology 3-(SH2/SH3) domain-containing gene and its encoded protein, called hSLAP-2, which was determined by homology analysis to be a member of the SLAP family of adapter proteins. The gene and encoded product according to the present invention are called hSLAP-2 (human Src-Like Adapter Protein-2) due to its similarity with both human SLAP (hSLAP) and mouse SLAP (mSLAP) sequences. The SLAP proteins have been shown to be negative regulators of intracellular signal transduction in several cell types, including T-cells (see: Roche, S. et al., (1998) Src-like adaptor protein (Slap) is a negative regulator of mitogenesis. *Curr. Biol.* 8:975-978; Tang, J. et al., (1999) SLAP, a dimeric adapter protein, plays a functional role in T cell receptor signaling. *Proc. Natl. Acad. Sci. USA* 96:9775-9780; and Sosinowski, T. et al., (2000) Src-like adaptor protein (SLAP) is a negative regulator of T cell receptor signaling. *J. Exp. Med.* 191:463-474).

hSLAP-2 Polynucleotides and Polypeptides

The present invention encompasses the nucleic acid sequence (SEQ ID NO:1) encoding the full-length hSLAP-2 polypeptide (SEQ ID NO:2) and the use of compositions comprising the hSLAP-2 polynucleotide or polypeptide in methods for screening for antagonists or inhibitors of the interaction of hSLAP-2 with cellular signaling components. Also encompassed by the invention is the use of the hSLAP-2 nucleic acid sequence and the hSLAP-2 polypeptide in methods for diagnosing, treating or preventing disorders or diseases associated with aberrant or uncontrolled cellular signal transduction or with hyperactive cells, particularly in cells of immunological origin, including B- and T-lymphocytes, monocytes, mast cells and the like. Immunological or inflammatory disorders such as rheumatoid arthritis, rejection of organ or tissue transplants, inflammatory bowel disorders; autoimmune diseases such as systemic lupus erythematosus and multiple sclerosis; pulmonary diseases including asthma and chronic obstructive pulmonary disorder; and cancer, are particular targets for treatment by the present invention, including inhibitors of hSLAP-2 polynucleotide and polypeptide function. In addition, the hSLAP-2 gene and polypeptide are useful for determining those cellular signaling molecules which associate with hSLAP-2 and which provide critical signals for cell activation, preferably, T-cell activation.

According to the present invention, nucleic acids encoding human hSLAP-2 protein was first identified as a PCR product in a human leukocyte cDNA library, as described in Example 1. In addition, upon screening a human leukocyte cDNA library with the GeneTrapper™ (Life Technologies, Inc.; Gaithersburg, Md.) primer, positive clones containing the novel sequence were also identified. End-sequencing analysis revealed that one of the clones (clone #13) contains the full-length coding region of the hSLAP-2 gene, as described in Example 1.

In one of its embodiments, the present invention encompasses a polypeptide comprising the amino acid sequence of SEQ ID NO:2 as shown in FIG. 2. The human hSLAP-2 polypeptide is 262 amino acids in length and shares amino acid sequence similarity to the SLAP family members, hSLAP and mSLAP as presented in FIG. 4.

The table of FIG. 4 shows the percent similarity/identity at the amino acid level between human SLAP and mouse SLAP protein; between human SLAP and human SLAP-2; and between mouse SLAP and human SLAP-2. Based on the comparative data, human SLAP-2 is determined to be a novel sequence from this family of adapter proteins.

A mouse SLAP protein was reported by Pandey et al. (Pandey, a. et al. (1995) Characterization of a novel Src-like adapter protein that associates with the Eck receptor tyrosine kinase. *J. Biol. Chem.* 270: 19201-19204), followed by the identification of a human counterpart SLAP gene (Angrist, M. et al. (1995) Chromosomal localization of the mouse Src-like adapter protein (Slap) gene and its putative human homologue SLA. *Genomics* 30: 623-625; Meijerink, P. H. et al. (1998). The gene for the human Src-like adapter protein (hSLAP) is located within the 64-kb intron of the thyroglobulin gene. *Eur. J. Biochem.* 254: 297-303). Mouse SLAP is predominantly expressed in lymphoid cells (Sosinowski, T. et al. (2000) Src-like adapter protein (SLAP) is a negative regulator of T cell receptor signaling. *J. Exptl. Med.* 191: 463-474), and hSLAP-2 has a similar expression pattern, as seen in FIG. 8.

Variants of the hSLAP-2 polypeptide are also encompassed by the present invention. A preferred hSLAP-2 variant has at least 75 to 80%, more preferably at least 85 to 90%, and even more preferably at least 90% amino acid sequence identity to the amino acid sequence (SEQ ID NO:2) disclosed herein, and which retains at least one biological, immunological, or other functional characteristic or activity of the hSLAP-2 polypeptide. Most preferred is a variant having at least 95% amino acid sequence identity to the amino acid sequence set forth in SEQ ID NO:2. An amino acid sequence variant of the hSLAP-2 protein can be categorized into one or more of three classes: substitutional, insertional, or deletional variants. Such variants are typically prepared by site-specific mutagenesis of nucleotides in the DNA encoding the hSLAP-2 protein, using cassette or PCR mutagenesis, or other techniques that are well known and practiced in the art, to produce DNA encoding the variant. Thereafter, the DNA is expressed in recombinant cell culture as described herein. Variant hSLAP-2 protein fragments having up to about 100-150 residues may be prepared by in vitro synthesis using conventional techniques.

Amino acid sequence variants are characterized by the predetermined nature of the variation, a feature that sets them apart from naturally occurring allelic or interspecies variations of the hSLAP-2 protein amino acid sequence. The variants typically exhibit the same qualitative biological activity as that of the naturally occurring analogue, although variants can also be selected having modified characteristics. While the site or region for introducing an amino acid sequence variation is predetermined, the mutation per se need not be predetermined. For example, in order to optimize the performance of a mutation at a given site, random mutagenesis may be performed at the target codon or region, and the expressed hSLAP-2 variants screened for the optimal combination of desired activity. Techniques for making substitution mutations at predetermined sites in DNA having a known sequence are well known, for example, M13 primer mutagenesis and PCR mutagenesis. Screening of the mutants is accomplished using assays of hSLAP-2 protein activities, for example, for binding domain mutations, competitive binding studies may be carried out.

Amino acid substitutions are typically of single residues; insertions usually are on the order of from one to twenty amino acids, although considerably larger insertions may be tolerated. Deletions range from about one to about 20 residues, although in some cases, deletions may be much larger. For example, preferred deletion variants include the deletion of one or more of the characteristic domains, i.e., the proline-rich region, or the SH2/SH3 domain.

Substitutions, deletions, insertions, or any combination thereof, may be used to arrive at a final hSLAP-2 derivative. Generally, these changes affect only a few amino acids to minimize the alteration of the molecule. However, larger changes may be tolerated in certain circumstances. When small alterations in the characteristics of the hSLAP-2 protein are desired or warranted, substitutions are generally made in accordance with the following table:

TABLE 1

| Original Residue | Exemplary Substitutions |
| --- | --- |
| Ala | Ser |
| Arg | Lys |

TABLE 1-continued

| Original Residue | Exemplary Substitutions |
|---|---|
| Asn | Gln, His |
| Asp | Glu |
| Cys | Ser |
| Gln | Asn |
| Glu | Asp |
| Gly | Pro |
| His | Asn, Gln |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Table 1. For example, substitutions may be made which more significantly affect the structure of the polypeptide backbone in the area of the alteration, for example, the alpha-helical, or beta-sheet structure; the charge or hydrophobicity of the molecule at the target site; or the bulk of the side chain. The substitutions which generally are expected to produce the greatest changes in the polypeptide's properties are those in which (a) a hydrophilic residue, e.g., seryl or threonyl, is substituted for (or by) a hydrophobic residue, e.g., leucyl, isoleucyl, phenylalanyl, valyl, or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) a residue that does not have a side chain, e.g., glycine.

While hSLAP-2 variants ordinarily exhibit the same qualitative biological activity or function, and elicit the same immune response, as the naturally occurring analogue, the variants are also selected to modify the characteristics of the hSLAP-2 protein as needed. Alternatively, the variant may be designed such that the biological activity of the hSLAP-2 protein is altered. For example, any or all of the domains may be altered, i.e., the SH2 and/or SH3 regions, and/or the amino- and carboxy-terminal regions outside of the SH2 and SH3 domains. For example, one or more of the tyrosine phosphorylation sites may be altered.

In another embodiment, the present invention encompasses polynucleotides which encode the hSLAP-2 polypeptide. Accordingly, any nucleic acid sequence which encodes the amino acid sequence of the hSLAP-2 polypeptide can be used to produce recombinant molecules that express hSLAP-2 protein. In a particular embodiment, the present invention encompasses the hSLAP-2 polynucleotide comprising the nucleic acid sequence of SEQ ID NO:1 and as shown in FIG. 1. More particularly, the present invention provides the cloned full-length hSLAP-2 cDNA, deposited at the American Type Culture Collection (ATCC), 10801 University Boulevard, Manassas, Va. 20110-2209 on Nov. 20, 2001 and under ATCC Accession No. PTA-3873 according to the terms of the Budapest Treaty.

As will be appreciated by the skilled practitioner in the art, the degeneracy of the genetic code results in the production of numerous nucleotide sequences encoding the hSLAP-2 polypeptide of the present invention. Some of the sequences bear minimal homology to the nucleotide sequences of any known and naturally occurring gene. Accordingly, the present invention contemplates each and every possible variation of nucleotide sequence that could be made by selecting combinations based on possible codon choices. These combinations are made in accordance with the standard triplet genetic code as applied to the nucleotide sequence of naturally occurring hSLAP-2, and all such variations are to be considered as being specifically disclosed.

Although nucleotide sequences which encode the hSLAP-2 polypeptide and its variants are preferably capable of hybridizing to the nucleotide sequence of the naturally occurring hSLAP-2 polypeptide under appropriately selected conditions of stringency, it may be advantageous to produce nucleotide sequences encoding the hSLAP-2 polypeptide, or its derivatives, which possess a substantially different codon usage. Codons may be selected to increase the rate at which expression of the peptide/polypeptide occurs in a particular prokaryotic or eukaryotic host in accordance with the frequency with which particular codons are utilized by the host, for example, in plant cells or yeast cells or amphibian cells. Other reasons for substantially altering the nucleotide sequence encoding the hSLAP-2 polypeptide, and its derivatives, without altering the encoded amino acid sequences include the production of mRNA transcripts having more desirable properties, such as a greater half-life, than transcripts produced from the naturally occurring sequence.

The present invention also encompasses production of DNA sequences, or portions thereof, which encode the hSLAP-2 polypeptide, and its derivatives, entirely by synthetic chemistry. After production, the synthetic sequence may be inserted into any of the many available expression vectors and cell systems using reagents that are well known and practiced by those in the art. Moreover, synthetic chemistry may be used to introduce mutations into a sequence encoding hSLAP-2 polypeptide, or any fragment thereof.

Also encompassed by the present invention are polynucleotide sequences that are capable of hybridizing to the claimed nucleotide sequence of hSLAP-2, such as that shown in SEQ ID NO:1, under various conditions of stringency. Hybridization conditions are typically based on the melting temperature (Tm) of the nucleic acid binding complex or probe (see, G. M. Wahl and S. L. Berger, 1987*; Methods Enzymol.,* 152:399-407 and A. R. Kimmel, 1987*; Methods of Enzymol.,* 152:507-511), and may be used at a defined stringency. For example, included in the present invention are sequences capable of hybridizing under moderately stringent conditions to the hSLAP-2 nucleic acid sequence of SEQ ID NO:1 and other sequences which are degenerate to those which encode the hSLAP-2 polypeptide (e.g., as a non-limiting example: prewashing solution of 2×SSC, 0.5% SDS, 1.0 mM EDTA, pH 8.0, and hybridization conditions of 50° C., 5×SSC, overnight).

In another embodiment of the present invention, polynucleotide sequences or fragments (peptides) thereof which encode the hSLAP-2 polypeptide may be used in recombinant DNA molecules to direct the expression of the hSLAP-2 polypeptide product, or fragments or functional equivalents thereof, in appropriate host cells. Because of the inherent degeneracy of the genetic code, other DNA sequences, which encode substantially the same or a functionally equivalent amino acid sequence, may be produced and these sequences may be used to express hSLAP-2 protein.

As will be appreciated by those having skill in the art, it may be advantageous to produce hSLAP-2 polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequence of the present invention can be engineered using methods generally known in the art in order to alter hSLAP-2 polypeptide-encoding sequences for a variety of reasons, including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, or introduce mutations, and the like.

In another embodiment of the present invention, natural, modified, or recombinant nucleic acid sequences, or a fragment thereof, encoding hSLAP-2 polypeptide may be ligated to a heterologous sequence to encode a fusion protein. For example, for screening peptide libraries for inhibitors or modulators of hSLAP-2 activity or binding, it may be useful to encode a chimeric hSLAP-2 protein that can be recognized by a commercially available antibody. A fusion protein may also be engineered to contain a cleavage site located between the hSLAP-2 protein-encoding sequence and the heterologous protein sequence, so that the hSLAP-2 protein may be cleaved and purified away from the heterologous moiety.

In another embodiment, sequences encoding the hSLAP-2 polypeptide may be synthesized in whole, or in part, using chemical methods well known in the art (see, for example, M. H. Caruthers et al., 1980, Nucl. Acids Res. Symp. Ser., 215-223 and Horn, T. et al., 1980, Nucl. Acids Res. Symp. Ser., 225-232). Alternatively, the protein itself may be produced using chemical methods to synthesize the amino acid sequence of the hSLAP-2 polypeptide, or a fragment or portion thereof. For example, peptide synthesis can be performed using various solid-phase techniques (J. Y. Roberge et al., 1995, Science, 269:202-204) and automated synthesis may be achieved, for example, using the ABI 431A Peptide Synthesizer (PE Biosystems).

The newly synthesized peptide can be substantially purified by preparative high performance liquid chromatography (e.g., T. Creighton, 1983, Proteins, Structures and Molecular Principles, WH Freeman and Co., New York, N.Y.), by reversed-phase high performance liquid chromatography, or other purification methods as are known in the art. The composition of the synthetic peptides may be confirmed by amino acid analysis or sequencing (e.g., the Edman degradation procedure; Creighton, supra). In addition, the amino acid sequence of the hSLAP-2 polypeptide or any portion thereof, may be altered during direct synthesis and/or combined using chemical methods with sequences from other proteins, or any part thereof, to produce a variant polypeptide.

Expression of Human hSLAP-2 Protein

To express a biologically active/functional hSLAP-2 polypeptide or peptide, the nucleotide sequences encoding the hSLAP-2 polypeptide, or functional equivalents, may be inserted into an appropriate expression vector, i.e., a vector which contains the necessary elements for the transcription and translation of the inserted coding sequence. Methods which are well known to those skilled in the art may be used to construct expression vectors containing sequences encoding the hSLAP-2 polypeptide and appropriate transcriptional and translational control elements. These methods include in vitro recombinant DNA techniques, synthetic techniques, and in vivo genetic recombination. Such techniques are described in J. Sambrook et al., 1989, Molecular Cloning, A Laboratory Manual, Cold Spring Harbor Press, Plainview, N.Y. and in F. M. Ausubel et al., 1989, Current Protocols in Molecular Biology, John Wiley & Sons, New York, N.Y.

A variety of expression vector/host systems may be utilized to contain and express sequences encoding the hSLAP-2 polypeptide. Such expression vector/host systems include, but are not limited to, microorganisms such as bacteria transformed with recombinant bacteriophage, plasmid, or cosmid DNA expression vectors; yeast or fungi transformed with yeast or fungal expression vectors; insect cell systems infected with virus expression vectors (e.g., baculovirus); plant cell systems transformed with virus expression vectors (e.g., cauliflower mosaic virus (CaMV) and tobacco mosaic virus (TMV)), or with bacterial expression vectors (e.g., Ti or pBR322 plasmids); or animal cell systems. The host cell employed is not limiting to the present invention.

"Control elements" or "regulatory sequences" are those non-translated regions of the vector, e.g., enhancers, promoters, 5' and 3' untranslated regions, which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene; La Jolla, Calif.) or PSPORT1 plasmid (Life Technologies), and the like, may be used. The baculovirus polyhedrin promoter may be used in insect cells. Promoters or enhancers derived from the genomes of plant cells (e.g., heat shock, RUBISCO; and storage protein genes), or from plant viruses (e.g., viral promoters or leader sequences), may be cloned into the vector. In mammalian cell systems, promoters from mammalian genes or from mammalian viruses are preferred. If it is necessary to generate a cell line that contains multiple copies of the sequence encoding hSLAP-2, vectors based on SV40 or EBV may be used with an appropriate selectable marker.

In bacterial systems, a number of expression vectors may be selected, depending upon the use intended for the expressed hSLAP-2 product. For example, when large quantities of expressed protein are needed for the induction of antibodies, vectors which direct high level expression of fusion proteins that are readily purified may be used. Such vectors include, but are not limited to, the multifunctional E. coli cloning and expression vectors such as BLUESCRIPT (Stratagene), in which the sequence encoding the hSLAP-2 polypeptide, or a peptide thereof, may be ligated into the vector in-frame with sequences for the amino-terminal Met and the subsequent 7 residues of β-galactosidase, so that a hybrid protein is produced; pIN vectors (See, G. Van Heeke and S. M. Schuster, 1989, *J. Biol. Chem.*, 264:5503-5509); and the like. pGEX vectors (Promega, Madison, Wis.) may also be used to express foreign polypeptides, as fusion proteins with glutathione S-transferase (GST). In addition, hSLAP-2 fusion proteins expressing a His tag may be generated, for example, in which SH2/SH3 domains from human hSLAP-2 cDNA are cloned into an expression vector linked to a poly-His tag (His).

In general, fusion proteins are soluble and can be easily purified from lysed cells. For GST-fusion proteins purification is performed by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used (for reviews, see F. M. Ausubel et al., supra, and Grant et al., 1987, *Methods Enzymol.*, 153:516-544).

Should plant expression vectors be desired and used, the expression of sequences encoding the hSLAP-2 polypeptide may be driven by any of a number of promoters. For example, viral promoters such as the 35S and 19S promoters of CaMV may be used alone or in combination with the omega leader sequence from TMV (N. Takamatsu, 1987, *EMBO J.*, 6:307-311). Alternatively, plant promoters such as the small subunit of RUBISCO, or heat shock promoters, may be used (G. Coruzzi et al., 1984, *EMBO J.*, 3:1671-1680; R. Broglie et al., 1984, *Science*, 224:838-843; and J. Winter et al., 1991, *Results Probl. Cell Differ.* 17:85-105). These constructs can be introduced into plant cells by direct DNA transformation or pathogen-mediated transfection. Such techniques are described in a number of generally available reviews (see, for example, S. Hobbs or L. E. Murry, In: McGraw Hill *Yearbook of Science and Technology* (1992) McGraw Hill, New York, N.Y.; pp. 191-196).

An insect system may also be used to express the hSLAP-2 polypeptide. For example, in one such system, *Autographa californica* nuclear polyhedrosis virus (AcNPV) is used as a vector to express foreign genes in *Spodoptera frugiperda* cells or in *Trichoplusia larvae*. The sequences encoding the hSLAP-2 polypeptide may be cloned into a non-essential region of the virus such as the polyhedrin gene and placed under control of the polyhedrin promoter. Successful insertion of the hSLAP-2 polypeptide will render the polyhedrin gene inactive and produce recombinant virus lacking coat protein. The recombinant viruses may then be used to infect, for example, *S. frugiperda* cells or *Trichoplusia larvae* in which the hSLAP-2 polypeptide product may be expressed (E. K. Engelhard et al., 1994, *Proc. Nat. Acad. Sci.*, 91:3224-3227).

In mammalian host cells, a number of viral-based expression systems may be utilized. In cases where an adenovirus is used as an expression vector, sequences encoding the hSLAP-2 polypeptide may be ligated into an adenovirus transcription/translation complex containing the late promoter and tripartite leader sequence. Insertion in a non-essential E1 or E3 region of the viral genome may be used to obtain a viable virus which is capable of expressing the hSLAP-2 polypeptide in infected host cells (J. Logan and T. Shenk, 1984, *Proc. Natl. Acad. Sci.*, 81:3655-3659). In addition, transcription enhancers, such as the Rous sarcoma virus (RSV) enhancer, may be used to increase expression in mammalian host cells.

Specific initiation signals may also be used to achieve more efficient translation of sequences encoding the hSLAP-2 polypeptide. Such signals include the ATG initiation codon and adjacent sequences. In cases where sequences encoding the hSLAP-2 polypeptide, its initiation codon, and upstream sequences are inserted into the appropriate expression vector, no additional transcriptional or translational control signals may be needed. However, in cases where only coding sequence, or a fragment thereof, is inserted, exogenous translational control signals, including the ATG initiation codon, should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system that is used, such as those described in the literature (D. Scharf et al., 1994, *Results Probl. Cell Differ.*, 20:125-162).

Moreover, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells having specific cellular machinery and characteristic mechanisms for such post-translational activities (e.g., COS, CHO, HeLa, MDCK, HEK293, and W138) are available from the American Type Culture Collection (ATCC), American Type Culture Collection (ATCC), 10801 University Boulevard, Manassas, Va. 20110-2209, and may be chosen to ensure the correct modification and processing of the foreign protein.

For long-term, high-yield production of recombinant proteins, stable expression is preferred. For example, cell lines which stably express the hSLAP-2 protein may be transformed using expression vectors which may contain viral origins of replication and/or endogenous expression elements and a selectable marker gene on the same, or on a separate, vector. Following the introduction of the vector, cells may be allowed to grow for 1-2 days in an enriched cell culture medium before they are switched to selective medium. The purpose of the selectable marker is to confer resistance to selection, and its presence allows the growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the Herpes Simplex Virus thymidine kinase (HSV TK), (M. Wigler et al., 1977, *Cell*, 11:223-32) and adenine phosphoribosyltransferase (I. Lowy et al., 1980, *Cell*, 22:817-23) genes which can be employed in tk$^-$ or aprt$^-$ cells, respectively. Also, anti-metabolite, antibiotic or herbicide resistance can be used as the basis for selection; for example, dhfr, which confers resistance to methotrexate (M. Wigler et al., 1980, *Proc. Natl. Acad. Sci.*, 77:3567-70); npt, which confers resistance to the aminoglycosides neomycin and G-418 (F. Colbere-Garapin et al., 1981, *J. Mol. Biol.*, 150:1-14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (S. C. Hartman and R. C. Mulligan, 1988, *Proc. Natl. Acad. Sci.*, 85:8047-51). Recently, the use of visible markers has gained popularity with such markers as the anthocyanins, β-glucuronidase and its substrate GUS, and luciferase and its substrate luciferin, which are widely used not only to identify transformants, but also to quantify the amount of transient or stable protein expression that is attributable to a specific vector system (C. A. Rhodes et al., 1995, *Methods Mol. Biol.*, 55:121-131).

Although the presence or absence of marker gene expression suggests that the gene of interest is also present, the presence and expression of the desired gene of interest may need to be confirmed. For example, if the hSLAP-2 nucleic acid sequence polypeptide is inserted within a marker gene sequence, recombinant cells containing sequences encoding the hSLAP-2 polypeptide can be identified by the absence of marker gene function. Alternatively, a marker gene can be placed in tandem with a sequence encoding the hSLAP-2 polypeptide under the control of a single promoter. Expression of the marker gene in response to induction or selection usually indicates co-expression of the tandem gene.

Alternatively, host cells which contain the nucleic acid sequence encoding the hSLAP-2 polypeptide and which express the hSLAP-2 polypeptide product may be identified by a variety of procedures known to those having skill in the art. These procedures include, but are not limited to, DNA-DNA or DNA-RNA hybridizations and protein bioassay or immunoassay techniques, including membrane, solution, or chip based technologies, for the detection and/or quantification of nucleic acid or protein.

Preferably, the hSLAP-2 polypeptide is substantially purified subsequent to expression. hSLAP-2 proteins can be isolated or purified in a variety of ways known to and practiced by those having skill in the art, depending on what other components may be present in the sample. Standard purification methods include electrophoretic, molecular, immunological and chromatographic techniques, including, but not limited to, ion exchange, hydrophobic affinity and reverse phase HPLC chromatography, and chromatofocusing. For example, the hSLAP-2 protein can be purified using a standard antibody against hSLAP-2 column. Ultrafiltration and diafiltration techniques, in conjunction with protein concentration, are also useful. For general guidance in suitable purification techniques, see R. Scopes, 1982, *Protein Purification*, Springer-Verlag, NY. As will be understood by the skilled practitioner, the degree of purification necessary will vary depending on the intended use of the hSLAP-2 protein; in some instances, no purification will be necessary.

In addition to recombinant production, fragments of the hSLAP-2 polypeptide may be produced by direct peptide synthesis using solid-phase techniques (J. Merrifield, 1963, *J. Am. Chem. Soc.*, 85:2149-2154). Protein synthesis may be performed using manual techniques or by automation. Automated synthesis may be achieved, for example, using ABI 431A Peptide Synthesizer (PE Biosystems). Various fragments of the hSLAP-2 polypeptide can be chemically synthesized separately and then combined using chemical methods to produce the full-length molecule.

Detection of Human hSLAP-2 Polynucleotide

The presence of polynucleotide sequences encoding the hSLAP-2 polypeptide can be detected by DNA-DNA or DNA-RNA hybridization, or by amplification using probes or portions or fragments of polynucleotides encoding the hSLAP-2 polypeptide. Nucleic acid amplification based assays involve the use of oligonucleotides or oligomers, based on the sequences encoding the hSLAP-2 polypeptide, to detect transformants containing DNA or RNA encoding the hSLAP-2 polypeptide.

A wide variety of labels and conjugation techniques are known and employed by those skilled in the art and may be used in various nucleic acid and amino acid assays. Means for producing labeled hybridization or PCR probes for detecting sequences related to polynucleotides encoding the hSLAP-2 polypeptide include oligo-labeling, nick translation, end-labeling, or PCR amplification using a labeled nucleotide. Alternatively, the sequences encoding the hSLAP-2 polypeptide, or any portions or fragments thereof, may be cloned into a vector for the production of an mRNA probe. Such vectors are known in the art, are commercially available, and may be used to synthesize RNA probes in vitro by addition of an appropriate RNA polymerase, such as T7, T3, or SP(6) and labeled nucleotides. These procedures may be conducted using a variety of commercially available kits (e.g., Amersham Pharmacia Biotech, Promega and U.S. Biochemical Corp.). Suitable reporter molecules or labels which may be used include radionuclides, enzymes, fluorescent, chemiluminescent, or chromogenic agents, as well as substrates, cofactors, inhibitors, magnetic particles, and the like.

In another of its aspects, this invention relates to a diagnostic kit for detecting hSLAP-2 polynucleotide or polypeptide as it relates to a disease or susceptibility to a disease, particularly autoimmune diseases which may be caused by hyperactivated B cells, as well as diseases which may be caused by hyperactivated T cells (e.g., rheumatoid arthritis; asthma; psoriasis; multiple sclerosis; rejection of organ or tissue transplants; chronic obstructive pulmonary disease; inflammatory bowel diseases, including Crohn's Disease and ulcerative colitis; acute respiratory distress syndrome; and systemic lupus erythematosus), or disorders associated with other types of hematopoietic cells, such as allergies involving mast cells, leukemias and lymphomas, or chronic obstructive pulmonary disorders (as supra). Such a kit comprises one or more of the following:

(a) a hSLAP-2 polynucleotide, preferably the nucleotide sequence of SEQ ID NO:1, or a fragment thereof; or (b) a nucleotide sequence complementary to that of (a); or (c) a hSLAP-2 polypeptide, preferably the polypeptide of SEQ ID NO: 2, or a fragment thereof; or (d) an antibody to a hSLAP-2 polypeptide, preferably to the polypeptide of SEQ ID NO: 2, or an antibody bindable portion thereof. It will be appreciated that in any such kit, (a), (b), (c) or (d) may comprise a substantial component and that instructions for use can be included.

Human hSLAP-2 Polypeptides—Production, Detection, Isolation

Host cells transformed with nucleotide sequences encoding the hSLAP-2 protein, or fragments thereof, may be cultured under conditions suitable for the expression and recovery of the protein from cell culture. The protein produced by a recombinant cell may be secreted or contained intracellularly depending on the sequence and/or the vector used. As will be understood by those having skill in the art, expression vectors containing polynucleotides which encode the hSLAP-2 protein may be designed to contain signal sequences which direct secretion of the hSLAP-2 protein through a prokaryotic or eukaryotic cell membrane.

Other constructions may be used to join nucleic acid sequences encoding the hSLAP-2 protein to nucleotide sequence encoding a polypeptide domain which will facilitate purification of soluble proteins. Such purification facilitating domains include, but are not limited to, metal chelating peptides such as histidine-tryptophan modules that allow purification on immobilized metals; protein A domains that allow purification on immobilized immunoglobulin; and the domain utilized in the FLAGS extension/affinity purification system (Immunex Corp.; Seattle, Wash.). The inclusion of cleavable linker sequences such as those specific for Factor XA or enterokinase (Invitrogen, San Diego, Calif.) between the purification domain and the hSLAP-2 protein may be used to facilitate purification.

One such expression vector provides for expression of a fusion protein containing hSLAP-2-encoding sequence and a nucleic acid encoding 6 histidine residues preceding a thioredoxin or an enterokinase cleavage site. The histidine residues facilitate purification on IMAC (immobilized metal ion affinity chromatography) as described by J. Porath et al., 1992, *Prot. Exp. Purif.*, 3:263-281, while the enterokinase cleavage site provides a means for purifying from the fusion protein. For a discussion of suitable vectors for fusion protein production, see D. J. Kroll et al., 1993; *DNA Cell Biol.*, 12:441-453.

Human artificial chromosomes (HACs) may be used to deliver larger fragments of DNA than can be contained and expressed in a plasmid vector. HACs are linear microchromosomes which may contain DNA sequences of 10K to 10M in size, and contain all of the elements that are required for stable mitotic chromosome segregation and maintenance (see, J. J. Harrington et al., 1997, *Nature Genet.*, 15:345-355). HACs of 6 to 10M are constructed and delivered via conventional delivery methods (e.g., liposomes, polycationic amino polymers, or vesicles) for therapeutic purposes.

A variety of protocols for detecting and measuring the expression of the hSLAP-2 polypeptide using either polyclonal or monoclonal antibodies specific for the protein are known and practiced in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive with two non-interfering epitopes on the hSLAP-2 polypeptide is preferred, but a competitive binding assay may also be employed. These and other assays are described in the art as represented by the publication of R. Hampton et al., 1990; *Serological Methods, a Laboratory Manual*, APS Press, St Paul, Minn. and D. E. Maddox et al., 1983; *J. Exp. Med.*, 158:1211-1216).

Antibodies Raised Against Human SLAP-2 and Uses Thereof

Antagonists or inhibitors of the hSLAP-2 polypeptide of the present invention may be produced using methods which are generally known in the art. In particular, purified hSLAP-2 protein, or fragments thereof, can be used to produce antibodies, or to screen libraries of pharmaceutical agents or other compounds, particularly, small molecules, synthetic or naturally occurring, to identify those which specifically bind hSLAP-2. (e.g. Libraries are commercially available from Sigma or Aldrich).

Antibodies specific for the hSLAP-2 polypeptide, or immunogenic peptide fragments thereof, can be generated using methods that have long been known and conventionally practiced in the art. Such antibodies may include, but are not limited to, polyclonal, monoclonal, chimeric, single chain, Fab fragments, and fragments produced by an Fab expression library. Neutralizing antibodies, (i.e., those which inhibit dimer formation) are especially preferred for therapeutic use.

For the production of antibodies, various hosts including goats, rabbits, sheep, rats, mice, humans, and others, can be immunized by injection with hSLAP-2 polypeptide, or any peptide fragment or oligopeptide thereof, which has immunogenic properties. Depending on the host species, various adjuvants may be used to increase the immunological response. Nonlimiting examples of suitable adjuvants include Freund's (incomplete), mineral gels such as aluminum hydroxide or silica, and surface-active substances such as lysolecithin, pluronic polyols, polyanions, peptides, oil emulsions, KLH, and dinitrophenol. Adjuvants typically used in humans include BCG (bacilli Calmette Guérin) and *Corynebacterium parvumn*.

Preferably, the peptides, fragments, or oligopeptides used to induce antibodies to hSLAP-2 polypeptide (i.e., immunogens) have an amino acid sequence having at least five amino acids, and more preferably, at least 7-10 amino acids. It is also preferable that the immunogens are identical to a portion of the amino acid sequence of the natural protein; they may also contain the entire amino acid sequence of a small, naturally occurring molecule. The peptides, fragments or oligopeptides may comprise a single epitope or antigenic determinant or multiple epitopes. Short stretches of hSLAP-2 amino acids may be fused with those of another protein, such as KLH, and antibodies are produced against the chimeric molecule.

Monoclonal antibodies to hSLAP-2 polypeptide, or immunogenic fragments thereof, may be prepared using any technique which provides for the production of antibody molecules by continuous cell lines in culture. These include, but are not limited to, the hybridoma technique, the human B-cell hybridoma technique, and the EBV-hybridoma technique (G. Kohler et al., 1975, *Nature*, 256:495-497; D. Kozbor et al., 1985, *J. Immunol. Methods*, 81:31-42; R. J. Cote et al., 1983, *Proc. Natl. Acad. Sci. USA*, 80:2026-2030; and S. P. Cole et al., 1984, *Mol. Cell Biol.*, 62:109-120). The production of monoclonal antibodies is well known and routinely used in the art.

According to the present invention, antibodies can be generated from various regions of the hSLAP-2 polypeptide. Discrete domains of the hSLAP-2 protein (e.g., the proline-rich domain, or a portion thereof, the residues of which are depicted in FIGS. 3A-3B and the SH2 and/or SH3 domain, or a portion thereof, the residues of which are also depicted in FIGS. 3A-3B), may also be suitable for use as immunogens to produce antibodies to human hSLAP-2.

In addition, techniques developed for the production of "chimeric antibodies," the splicing of mouse antibody genes to human antibody genes to obtain a molecule with appropriate antigen specificity and biological activity can be used (S. L. Morrison et al., 1984, *Proc. Natl. Acad. Sci. USA*, 81:6851-6855; M. S. Neuberger et al., 1984, *Nature*, 312:604-608; and S. Takeda et al., 1985, *Nature*, 314:452-454). Alternatively, techniques described for the production of single chain antibodies may be adapted, using methods known in the art, to produce hSLAP-2 polypeptide-specific single chain antibodies. Antibodies with related specificity, but of distinct idiotypic composition, may be generated by chain shuffling from random combinatorial immunoglobulin libraries (D. R. Burton, 1991, *Proc. Natl. Acad. Sci. USA*, 88:11120-3). Antibodies may also be produced by inducing in vivo production in the lymphocyte population or by screening recombinant immunoglobulin libraries or panels of highly specific binding reagents as disclosed in the literature (R. Orlandi et al., 1989, *Proc. Natl. Acad. Sci. USA*, 86:3833-3837 and G. Winter et al., 1991, *Nature*, 349:293-299).

Antibody fragments which contain specific binding sites for the hSLAP-2 polypeptide may also be generated. For example, such fragments include, but are not limited to, $F(ab')_2$ fragments which can be produced by pepsin digestion of the antibody molecule and Fab fragments which can be generated by reducing the disulfide bridges of the $F(ab')_2$ fragments. Alternatively, Fab expression libraries may be constructed to allow rapid and easy identification of monoclonal Fab fragments with the desired specificity (W. D. Huse et al., 1989, *Science,* 254.1275-1281).

Various immunoassays can be used for screening to identify antibodies having the desired specificity. Numerous protocols for competitive binding or immunoradiometric assays using either polyclonal or monoclonal antibodies with established specificities are well known in the art. Such immunoassays typically involve measuring the formation of complexes between the hSLAP-2 polypeptide and its specific antibody. A two-site, monoclonal-based immunoassay utilizing monoclonal antibodies reactive with two non-interfering hSLAP-2 polypeptide epitopes is preferred, but a competitive binding assay may also be employed (Maddox, supra).

Therapeutics/Treatments

In an embodiment of the present invention, the polynucleotide encoding the hSLAP-2 polypeptide, or any fragment or complement thereof, may be used for therapeutic purposes. In one aspect, anti-sense to the polynucleotide encoding the hSLAP-2 polypeptide may be used in situations in which it would be desirable to block translation of the mRNA. In particular, cells may be transformed with sequences complementary to polynucleotides encoding the hSLAP-2 polypeptide. Thus, complementary molecules may be used to modulate human hSLAP-2 polynucleotide and polypeptide activity, or to achieve regulation of gene function. Such technology is now well known in the art, and sense or anti-sense oligomers or oligonucleotides, or larger fragments, can be designed from various locations along the coding or control regions of polynucleotide sequences encoding the hSLAP-2 polypeptide.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express nucleic acid sequence that is complementary to the nucleic acid sequence encoding the hSLAP-2 polypeptide. These techniques are described both in J. Sambrook et al., supra and in F. M. Ausubel et al., supra.

The gene encoding the hSLAP-2 polypeptide can be turned off by transforming a cell or tissue with an expression vector that expresses high levels of a hSLAP-2 polypeptide-encoding polynucleotide, or a fragment thereof. Such constructs may be used to introduce untranslatable sense or anti-sense sequences into a cell. Even in the absence of integration into the DNA, such vectors may continue to transcribe RNA molecules until they are disabled by endogenous nucleases. Transient expression may last for a month or more with a non-replicating vector, and even longer if appropriate replication elements are designed to be part of the vector system.

Modifications of gene expression can be obtained by designing anti-sense molecules or complementary nucleic acid sequences (DNA, RNA, or PNA), to the control, 5', or regulatory regions of the gene encoding the hSLAP-2 polypeptide, (e.g., signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described (see, for example, J. E. Gee et al., 1994, In: B. E. Huber and B. I. Carr, *Molecular and Immunologic Approaches,* Futura Publishing Co.; Mt. Kisco, N.Y.). The anti-sense molecule or complementary sequence may also be designed to block translation of mRNA by preventing the transcript from binding to ribosomes.

Ribozymes, i.e., enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Suitable examples include engineered hammerhead motif ribozyme molecules that can specifically and efficiently catalyze endonucleolytic cleavage of sequences encoding the hSLAP-2 polypeptide.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes according to the invention may be prepared by any method known in the art for the synthesis of nucleic acid molecules. Such methods include techniques for chemically synthesizing oligonucleotides, for example, solid phase phosphoramidite chemical synthesis. Alternatively, RNA molecules may be generated by in vitro and in vivo transcription of DNA sequences encoding human hSLAP-2. Such DNA sequences may be incorporated into a wide variety of vectors with suitable RNA polymerase promoters such as T7 or SP. Alternatively, the cDNA constructs that constitutively or inducibly synthesize complementary hSLAP-2 RNA can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl, rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytosine, guanine, thymine, and uridine which are not as easily recognized by endogenous endonucleases.

Many methods for introducing vectors into cells or tissues are available and are equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

The SH2 domain of SLAP was shown to bind to phosphorylated tyrosine residues in ZAP-70, Syk, and LAT (Tang, J. et al. (1999) *Proc. Natl. Acad. Sci., USA.* 96: 9775-9780), and possibly other signaling proteins (Sosinowski, T. et al. (2000) *J. Exptl. Med.* 191: 463-474). The SH3 domain of SLAP was determined to most likely bind proline rich (PR) motifs, which may help to transmit important intracellular signals in many cell types. Seven tyrosine residues in the coding sequence of hSLAP-2 may be sites of phosphorylation by (a)

tyrosine kinase(s). Such phosphorylated tyrosine residues may be important for binding to other SH2- or PTB domains involved in cell regulation.

In another embodiment of the present invention, an expression vector containing the complement of the polynucleotide encoding the hSLAP-2 polypeptide or an anti-sense oligonucleotide, may be administered to an individual to treat or prevent immune system related conditions, diseases, or disorders, T-cell and B-cell neoplasms; inflammation disorders, diseases and conditions, rheumatoid arthritis, osteoarthritis, psoriasis, rhinitis, inflammatory bowel disease (Crohn's and ulcerative colitis), allergies, particularly those involving hyperactivity of B-cells and T-cells, or other immune cells, such as mast cells or eosinophils; autoimmune diseases such as systemic lupus erythematosus and multiple sclerosis; pulmonary diseases including asthma, acute respiratory distress syndrome, and chronic obstructive pulmonary disorder; tissue/organ rejection; and cancer.

A variety of specialized oligonucleotide delivery techniques may be employed, for example, encapsulation in unilamellar liposomes and reconstituted Sendai virus envelopes for RNA and DNA delivery (Arad et al., 1986, *Biochem. Biophys. Acta.*, 859:88-94).

In another embodiment, the proteins, antagonists, antibodies, intracellular antibodies, agonists, complementary sequences, or vectors of the present invention can be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Any of the therapeutic methods described above may be applied to any individual in need of such therapy, including, for example, mammals such as dogs, cats, cows, horses, rabbits, monkeys, and most preferably, humans.

Screening Methods

The hSLAP-2 protein and nucleic acid can be used in screening assays of candidate bioactive agents that modulate hSLAP-2 bioactivity, for potential use to treat T- and B-cell disorders, such as tumors, lymphomas, and leukemias, or to treat inflammation disorders, such as those involving T-cells. In addition, hSLAP-2 protein and encoding nucleic acid can be used as effectors in methods to affect T-cell activation. By "modulate" herein is meant that the bioactivity of hSLAP-2 is altered, i.e., either increased or decreased. In a preferred embodiment, hSLAP-2 bioactivity is inhibited. hSLAP-2 is a member of the class of adapter proteins involved in T-cell activation and T-cell responses; thus, it may play a role in antigen-presenting cells such as B-cells. Accordingly, hSLAP-2 can be used as a target to screen for inhibitors of its function or expression.

Inhibitors of human hSLAP-2 may be identified by screening compounds to ascertain their effect on hSLAP-2 activity. As described herein, in some embodiments of the present invention, compounds are screened to identify inhibitors by contacting human hSLAP-2 with a molecule with which it binds or associates, (e.g., possibly ZAP-70, Syk, and LAT as suggested by published data with the SLAP protein; Tang, J. et al. (1999) *Proc. Natl. Acad Sci. USA* 96:9775-9780), in the presence or absence of a test compound. Under conditions of the assay, the inhibitors will prevent or reduce binding of human hSLAP-2 to ZAP-70, for example. Antibodies which inhibit hSLAP-2/ZAP-70 binding are useful as inhibitors and, therefore as positive controls in the assay.

In a similar fashion, activators of human SLAP-2 may be identified by screening compounds to ascertain their effect on hSLAP-2/ZAP-70 binding, for example. In some embodiments of the present invention, compounds are screened to identify activators by contacting human SLAP-2 with ZAP-70 in the presence or absence of a test compound. Under conditions of the assay, the activators will enhance, accelerate or increase binding of human hSLAP-2 to ZAP-70. Antibodies which inhibit hSLAP-2/ZAP-70 binding are useful as negative controls in such assays.

In another embodiment, an assay is provided to identify compounds that inhibit the phosphorylation of hSLAP-2 by tyrosine kinases such as, for example but not limited to, certain cellular receptors. In one aspect, hSLAP-2 is bound to solid substrate and the reaction buffer contains $^{32}$P-gamma-ATP. Tyrosine kinase is added in the presence or absence of a test compound. Test compounds are identified that result in a decrease in the amount of $^{32}$P label that is incorporated into hSLAP-2, compared with the level of phosphorylation observed in their absence. Kits are provided which comprise a container with hSLAP-2 fixed to a solid phase, a container with the reaction buffer, optionally containing $^{32}$P-gamma-ATP, and a container with tyrosine kinase. Kits may optionally have positive and/or negative controls. Such kits typically also have instructions for performing such assays.

In another embodiment of the present invention, hSLAP-2 proteins and nucleic acids are used in screening assays to identify and detect candidate bioactive agents that modulate hSLAP-2 bioactivity, for potential use to treat autoimmune diseases which may be caused by hyperactivated B cells, as well as to treat diseases which may be caused by hyperactivated T cells, in addition to other immune system related conditions, diseases, or disorders, T-cell and B-cell neoplasms; inflammation disorders, diseases and conditions, rheumatoid arthritis, osteoarthritis, psoriasis, rhinitis, inflammatory bowel disease (Crohn's and ulcerative colitis), allergies, particularly those involving hyperactivity of B-cells and T-cells, or other immune cells, such as mast cells or eosinophils; autoimmune diseases such as systemic lupus erythematosus and multiple sclerosis; pulmonary diseases including asthma, acute respiratory distress syndrome, and chronic obstructive pulmonary disorder; tissue/organ rejection; and cancer.

In a related embodiment, the methods comprise screening for a bioactive agent capable of inhibiting the bioactivity of a hSLAP-2 protein. By "bioactivity" herein is meant the binding of the hSLAP-2 to any of its targets, for example, including ZAP-70, Syk, and LAT, as suggested by published data with SLAP protein. Thus, bioactive agents that prevent hSLAP-2 binding, i.e., interrupt or block or inhibit the interaction of hSLAP-2 and its target molecule, may be found. The method comprises combining the hSLAP-2 protein and a candidate bioactive agent, and determining the binding of the candidate agent to hSLAP-2 protein.

Generally, in performing such methods, a hSLAP-2 polypeptide is non-diffusably bound to an insoluble support having isolated sample receiving areas (e.g. a microtiter plate, an array, etc.). The criteria for suitable insoluble supports are that they can be made of any composition to which polypeptides can be bound, they are readily separated from soluble material, and they are otherwise compatible with the overall method of screening. The surface of such supports may be solid or porous and of any convenient size or shape. Examples of suitable insoluble supports include microtiter plates, arrays, membranes and beads. These are typically made of glass, plastic (e.g., polystyrene), polysaccharides, nylon or nitrocellulose. Microtiter plates and arrays are especially convenient, because a large number of assays can be carried out simultaneously, using small amounts of reagents and samples. The particular manner of binding the polypeptide is not crucial, so long as it is compatible with the reagents and overall methods of the invention, maintains the activity of the peptide and is non-diffusable. Preferred methods of binding include the use of antibodies (which should not hinder the binding of hSLAP-2 to its associated proteins), direct binding to "sticky" or ionic supports, chemical crosslinking, etc. Following binding of the polypeptide, excess unbound material is removed by washing. The sample receiving areas may then be blocked as needed through incubation with bovine serum albumin (BSA), casein or other innocuous/non-reactive protein.

A candidate bioactive agent is added to the assay. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, and the like. The term "agent" as used herein describes any molecule, e.g., protein, oligopeptide, small organic molecule, polysaccharide, polynucleotide, etc., having the capability of directly or indirectly altering the bioactivity of hSLAP-2 proteins. Generally a plurality of assay mixtures are run in parallel with different agent concentrations to obtain a differential response to the various concentrations. Typically, one of these concentrations serves as a negative control, i.e., at zero concentration, or below the level of detection.

Candidate agents encompass numerous chemical classes, though typically they are organic molecules, preferably small organic compounds having a molecular weight of more than 100 and less than about 10,000 daltons, preferably less than about 2000 to 5000 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. In addition, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

The determination of the binding of the candidate bioactive agent to the hSLAP-2 polypeptide may be accomplished in a number of ways practiced in the art. In one aspect, the candidate bioactive agent is labeled, and binding is determined directly. Where the screening assay is a binding assay, one or more of the molecules may be joined to a label, where the label can directly or indirectly provide a detectable signal. Various labels include radioisotopes, fluorescent and chemiluminescent compounds, specific binding molecules, particles, e.g. magnetic particles, and the like. Specific binding molecules include pairs, such as biotin and streptavidin, digoxin and antidigoxin etc. For the specific-binding members, the complementary member would normally be labeled with a molecule which allows detection, in accordance with known procedures. In some embodiments, only one of the components is labeled. Alternatively, more than one component may be labeled with different labels; for example, the hSLAP-2 polypeptide may be labeled with one fluorophor and the candidate agent labeled with another In one embodiment, the candidate bioactive agent is labeled. Labeled candidate bioactive agents are incubated with the hSLAP-2 polypeptide for a time sufficient to allow binding, if present. Incubations may be performed at any temperature which facilitates optimal activity, typically between 4° C. and 40° C. Incubation periods are selected for optimum activity, but may also be optimized to facilitate rapid high throughput screening. Typically between 0.1 and 1 hour is sufficient. Excess reagent is generally removed or washed away. The presence or absence of the labeled component is detected to determine and indicate binding.

In a preferred embodiment, the screening method comprises combining a hSLAP-2 protein, a candidate bioactive agent, and either ZAP-70 or another of the signaling proteins that associate with hSLAP-2 (e.g., Syk, LAT), and determining the binding of hSLAP-2 to either ZAP-70 or other signaling protein to determine the effect of the candidate bioactive agent on the hSLAP-2-signaling protein interaction.

Another embodiment of this invention encompasses small molecule (e.g., drug) or compound screening and detection assays which involve the detection or identification of small molecules or compounds that can bind to a given protein, i.e., the hSLAP-2 protein. Particularly preferred are assays suitable for high throughput screening methodologies. In such binding-based screening or detection assays, a functional assay is not typically required. All that is needed is a target protein, preferably substantially purified, and a library or panel of compounds (e.g., ligands, drugs, small molecules) to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, *Gen. Eng. News,* 20(8)). The assay allows the detection of small molecules (e.g., drugs, ligands) that bind to expressed, and preferably purified, hSLAP-2 polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

In a differential screening method to identity bioactive agents that are capable of modulating the bioactivity of the hSLAP-2 protein, hSLAP-2 polypeptide is combined with either ZAP-70 or another signaling molecule which interacts with hSLAP-2 in a first sample. A second sample comprises a candidate bioactive agent, hSLAP-2 polypeptide and either ZAP-70 or other hSLAP-2 interacting signaling molecule. The binding of hSLAP-2 to either ZAP-70 or other signaling molecule is determined for both samples, and a change, or difference in binding, between the two samples indicates the presence of an agent capable of modulating the bioactivity of hSLAP-2. Alternatively, a differential screening method is utilized to identify drug candidates that bind to the native hSLAP-2, but cannot bind to modified hSLAP-2 proteins, or variant hSLAP-2 proteins, for example, those that have modifications which eliminate or decrease bioactivity of a hSLAP-2 protein.

Preferably in such methods, all control and test samples are performed in at least triplicate to obtain statistically significant results. Incubation of all samples is for a time sufficient for the binding of the hSLAP-2 proteins and the ZAP-70 and/or other signaling protein. Following incubation, all samples are washed free of non-specifically bound material and the amount of bound, labeled material determined. For example, where a radiolabel is employed as a label, the samples may be counted in a scintillation counter to determine the amount of labeled compound.

A variety of other reagents may be included in the screening assay. Such reagents include, but are not limited to, salts, neutral proteins, e.g. albumin, detergents, etc., which may be used to facilitate optimal protein-protein binding and/or reduce non-specific or background interactions. In addition, reagents that otherwise improve the efficiency of the assay, such as protease inhibitors, nuclease inhibitors, anti-microbial agents, etc. may be used. Further, the mixture of components in the method may be added in any order that provides for the requisite binding.

Kits are included as an embodiment of the present invention which comprise containers with reagents necessary to screen test compounds. Such kits include human hSLAP-2 and instructions for performing the assay. For example, kits may include means to detect and/or measure human hSLAP-2 binding using antibodies that bind to human hSLAP-2/ZAP-70 complex, but not to uncomplexed proteins, or antibodies that bind to uncomplexed proteins but not the human hSLAP-2/ZAP-70 complex. Optionally antibodies raised against human hSLAP-2 are provided as a control.

Pharmaceutical Compositions

A further embodiment of the present invention embraces the administration of a pharmaceutical composition, in conjunction with a pharmaceutically acceptable carrier, diluent, or excipient, for any of the above-described therapeutic uses and effects. Such pharmaceutical compositions may comprise hSLAP-2 nucleic acid, polypeptide, or peptides, antibodies to hSLAP-2 polypeptide, or fragments thereof, mimetics, agonists (e.g., activators), antagonists (e.g., inhibitors) of the hSLAP-2 polypeptide or polynucleotide. The compositions may be administered alone or in combination with at least one other agent, such as a stabilizing compound, which may be administered in any sterile, biocompatible pharmaceutical carrier, including, but not limited to, saline, buffered saline, dextrose, and water. The compositions may be administered to a patient alone, or in combination with other agents, drugs, hormones, or biological response modifiers.

The pharmaceutical compositions for use in the present invention can be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, vaginal, or rectal means.

In addition to the active ingredients (i.e., the hSLAP-2 nucleic acid or polypeptide, or functional fragments thereof), the pharmaceutical compositions may contain suitable pharmaceutically acceptable carriers or excipients comprising auxiliaries which facilitate processing of the active compounds into preparations which can be used pharmaceutically. Further details on techniques for formulation and administration are provided in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained by the combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropyl-methylcellulose, or sodium carboxymethylcellulose; gums, including arabic and tragacanth, and proteins such as gelatin and collagen. If desired, disintegrating or solubilizing agents may be added, such as cross-linked polyvinyl pyrrolidone, agar, alginic acid, or a physiologically acceptable salt thereof, such as sodium alginate.

Dragee cores may be used in conjunction with physiologically suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification, or to characterize the quantity of active compound, i.e., dosage.

Pharmaceutical preparations, which can be used orally, include push-fit capsules made of gelatin, as well as soft, scaled capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. In addition, suspensions of the active compounds may be prepared as appropriate oily injection suspensions. Suitable lipophilic solvents or vehicles include fatty oils such as sesame oil, or synthetic fatty acid esters, such as ethyloleate or triglycerides, or liposomes. Optionally, the suspension may also contain suitable stabilizers or agents which increase the solubility of the compounds to allow for the preparation of highly concentrated solutions.

For topical or nasal administration, penetrants or permeation agents that are appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, and the like. Salts tend to be more soluble in aqueous solvents, or other protonic solvents, than are the corresponding free base forms. In other cases, the preferred preparation may be a lyophilized powder which may contain any or all of the following: 1-50 mM histidine, 0.1%-2% sucrose, and 2-7% mannitol, at a pH range of 4.5 to 5.5, combined with a buffer prior to use. After the pharmaceutical compositions have been prepared, they can be placed in an appropriate container and labeled for treatment of an indicated condition. For administration of the hSLAP-2 product, such labeling would include amount, frequency, and method of administration.

Pharmaceutical compositions suitable for use in the present invention include compositions wherein the active ingredients are contained in an effective amount to achieve the intended purpose. The determination of an effective dose or amount is well within the capability of those skilled in the art. For any compound, the therapeutically effective dose can be estimated initially either in cell culture assays, e.g., using neoplastic cells, or in animal models, usually mice, rabbits, dogs, or pigs. The animal model may also be used to determine the appropriate concentration range and route of administration. Such information can then be used and extrapolated to determine useful doses and routes for administration in humans.

A therapeutically effective dose refers to that amount of active ingredient, for example, the hSLAP-2 polypeptide, or active fragments thereof, antibodies to the hSLAP-2 polypeptide, agonists or antagonists of the hSLAP-2 polypeptide, which ameliorates, reduces, or eliminates the symptoms or condition. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio of toxic to therapeutic effects is the therapeutic index, which can be expressed as the ratio, $LD_{50}/ED_{50}$. Pharmaceutical compositions which exhibit large therapeutic indices are preferred. The data obtained from cell culture assays and animal studies are used in determining a range of dosages for human use. Preferred dosage contained in a pharmaceutical composition is within a range of circulating concentrations that include the ED50 with little or no toxicity. The dosage varies within this range depending upon the dosage form employed, sensitivity of the patient, and the route of administration.

The exact dosage will be determined by the practitioner, who will consider the factors related to the individual requiring treatment. Dosage and administration are adjusted to provide sufficient levels of the active moiety or to maintain the desired effect. Factors which may be taken into account include the severity of the individual's disease state, general health of the patient, age, weight, and gender of the patient, diet, time and frequency of administration, drug combination(s), reaction sensitivities, and tolerance/response to therapy. As a general guide, long-acting pharmaceutical compositions may be administered every 3 to 4 days, every week, or once every two weeks, depending on half-life and clearance rate of the particular formulation.

Normal dosage amounts may vary from 0.1 to 100,000 micrograms (µg), up to a total dose of about 1 gram (g), depending upon the route of administration. Guidance as to particular dosages and methods of delivery is provided in the literature and is generally available to practitioners in the art. Those skilled in the art will employ different formulations for nucleotides than for proteins or their inhibitors. Similarly, delivery of polynucleotides or polypeptides will be specific to particular cells, conditions, locations, and the like.

Assays and Diagnostics

In another embodiment of the present invention, antibodies which specifically bind to the hSLAP-2 polypeptide may be used for the diagnosis of conditions or diseases characterized by expression (or overexpression) of the hSLAP-2 polynucleotide or polypeptide, or in assays to monitor patients being treated with hSLAP-2 polypeptide, or its agonists, antagonists, or inhibitors. The antibodies useful for diagnostic purposes may be prepared in the same manner as those described above for use in therapeutic methods. Diagnostic assays for the hSLAP-2 polypeptide include methods which utilize the antibody and a label to detect the protein in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

Several assay protocols including ELISA, RIA, and FACS for measuring the hSLAP-2 polypeptide are known in the art and provide a basis for diagnosing altered or abnormal levels of hSLAP-2 polypeptide expression. Normal or standard values for hSLAP-2 polypeptide expression are established by combining body fluids or cell extracts taken from normal mammalian subjects, preferably human, with antibody to the hSLAP-2 polypeptide under conditions suitable for complex formation. The amount of standard complex formation may be quantified by various methods; photometric means are preferred. Quantities of the hSLAP-2 polypeptide expressed in subject sample, control sample, and disease samples from biopsied tissues are compared with the standard values. Deviation between standard and subject values establishes the parameters for diagnosing disease.

According to another embodiment of the present invention, the polynucleotides encoding hSLAP-2 polypeptide may be used for diagnostic purposes. The polynucleotides which may be used include oligonucleotide sequences, complementary RNA and DNA molecules, and PNAs. The polynucleotides may be used to detect and quantify hSLAP-2-encoding nucleic acid expression in biopsied tissues in which expression (or under- or over-expression) of hSLAP-2 polynucleotide may be correlated with disease. The diagnostic assay may be used to distinguish between the absence, presence, and excess expression of hSLAP-2, and to monitor regulation of hSLAP-2 polynucleotide levels during therapeutic treatment or intervention.

In a related aspect, hybridization with PCR probes which are capable of detecting polynucleotide sequences, including genomic sequences, encoding hSLAP-2 polypeptide, or closely related molecules, may be used to identify nucleic acid sequences which encode the hSLAP-2 polypeptide. The specificity of the probe, whether it is made from a highly specific region, e.g., about 8 to 10 or 12 or 15 contiguous nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding the hSLAP-2 polypeptide, alleles thereof, or related sequences.

Probes may also be used for the detection of related sequences, and should preferably contain at least 50%, preferably greater than 80%, of the nucleotides encoding hSLAP-2 polypeptide. The hybridization probes of this invention may be DNA or RNA and may be derived from the nucleotide sequence of SEQ ID NO:1, or from genomic sequence including promoter, enhancer elements, and introns of the naturally occurring hSLAP-2 protein.

Methods for producing specific hybridization probes for DNA encoding the hSLAP-2 polypeptide include the cloning of nucleic acid sequence that encodes the hSLAP-2 polypeptide, or hSLAP-2 derivatives, into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of detector/reporter groups, e.g., radionuclides such as $^{32}$P or $^{35}$S, or enzymatic labels, such as alkaline phosphatase coupled to the probe via avidin/biotin coupling systems, and the like.

The polynucleotide sequence encoding the hSLAP-2 polypeptide may be used in Southern or Northern analysis, dot blot, or other membrane-based technologies; in PCR technologies; or in dip stick, pin, ELISA or chip assays utilizing fluids or tissues from patient biopsies to detect the status of, e.g., levels or overexpression of hSLAP-2, or to detect altered hSLAP-2 expression. Such qualitative or quantitative methods are well known in the art.

In a particular aspect, the nucleotide sequence encoding the hSLAP-2 polypeptide may be useful in assays that detect activation or induction of various B- and T-cell-related neoplasms or cancers, particularly those mentioned supra. The nucleotide sequence encoding the hSLAP-2 polypeptide may be labeled by standard methods, and added to a fluid or tissue sample from a patient under conditions suitable for the formation of hybridization complexes. After a suitable incubation period, the sample is washed and the signal is quantified and compared with a standard value. If the amount of signal in the biopsied or extracted sample is significantly altered from that of a comparable control sample, the nucleotide sequence has hybridized with nucleotide sequence present in the sample, and the presence of altered levels of nucleotide sequence encoding the hSLAP-2 polypeptide in the sample indicates the presence of the associated disease. Such assays may also be used to evaluate the efficacy of a particular therapeutic treatment regimen in animal studies, in clinical trials, or in monitoring the treatment of an individual patient.

To provide a basis for the diagnosis of disease associated with expression of hSLAP-2, a normal or standard profile for expression is established. This may be accomplished by combining body fluids or cell extracts taken from normal subjects, either animal or human, with a sequence, or a fragment thereof, which encodes the hSLAP-2 polypeptide, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject (patient) values is used to establish the presence of disease.

Once disease is established and a treatment protocol is initiated, hybridization assays may be repeated on a regular basis to evaluate whether the level of expression in the patient begins to approximate that which is observed in a normal individual. The results obtained from successive assays may be used to show the efficacy of treatment over a period ranging from several days to months.

With respect to cancer, the presence of an abnormal amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier, thereby preventing the development or further progression of the cancer.

Additional diagnostic uses for oligonucleotides designed from the nucleic acid sequence encoding the hSLAP-2 polypeptide may involve the use of PCR. Such oligomers may be chemically synthesized, generated enzymatically, or produced from a recombinant source. Oligomers will preferably comprise two nucleotide sequences, one with sense orientation (5'→3') and another with anti-sense (3'→5'), employed under optimized conditions for identification of a specific gene or condition. The same two oligomers, nested sets of oligomers, or even a degenerate pool of oligomers may be employed under less stringent conditions for detection and/or quantification of closely related DNA or RNA sequences.

Methods suitable for quantifying the expression of hSLAP-2 include radiolabeling or biotinylating nucleotides, co-amplification of a control nucleic acid, and standard curves onto which the experimental results are interpolated (P. C. Melby et al., 1993, *J. Immunol. Methods,* 159:235-244; and C. Duplaa et al., 1993, *Anal. Biochem.,* 229-236). The speed of quantifying multiple samples may be accelerated by running the assay in an ELISA format where the oligomer of interest is presented in various dilutions and a spectrophotometric or colorimetric response gives rapid quantification.

In another embodiment of the present invention, oligonucleotides, or longer fragments derived from the hSLAP-2 polynucleotide sequence described herein may be used as targets in a microarray. The microarray can be used to monitor the expression level of large numbers of genes simultaneously (to produce a transcript image), and to identify genetic variants, mutations and polymorphisms. This information may be used to determine gene function, to understand the genetic basis of a disease, to diagnose disease, and to develop and monitor the activities of therapeutic agents. In a particular aspect, the microarray is prepared and used according to the methods described in WO 95/11995 (Chee et al.); D. J. Lockhart et al., 1996, *Nature Biotechnology,* 14:1675-1680; and M. Schena et al., 1996, *Proc. Natl. Acad. Sci. USA,* 93:10614-10619). Microarrays are further described in U.S. Pat. No. 6,015,702 to P. Lal et al.

In another embodiment of this invention, the nucleic acid sequence which encodes the hSLAP-2 polypeptide may also be used to generate hybridization probes which are useful for mapping the naturally occurring genomic sequence. The sequences may be mapped to a particular chromosome, to a specific region of a chromosome, or to artificial chromosome constructions (HACs), yeast artificial chromosomes (YACs), bacterial artificial chromosomes (BACs), bacterial PI constructions, or single chromosome cDNA libraries, as reviewed by C. M. Price, 1993, *Blood Rev.,* 7:127-134 and by B. J. Trask, 1991, *Trends Genet.,* 7:149-154.

In another embodiment of the present invention, the hSLAP-2 polypeptide, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between the hSLAP-2 polypeptide, or portion thereof, and the agent being tested, may be measured utilizing techniques commonly practiced in the art and as described above.

Another technique for drug screening which may be used provides for high throughput screening of compounds having suitable binding affinity to the protein of interest, for example, as described in WO 84/03564. In this method, as applied to the hSLAP-2 protein, large numbers of different small test compounds are synthesized on a solid substrate, such as plastic pins or some other surface. The test compounds are reacted with the hSLAP-2 polypeptide, or fragments thereof, and washed. Bound hSLAP-2 polypeptide is then detected by methods well known in the art. Purified hSLAP-2 polypeptide can also be coated directly onto plates for use in the aforementioned drug screening techniques. Alternatively, non-neutralizing antibodies can be used to capture the peptide and immobilize it on a solid support.

In a further embodiment of this invention, competitive drug screening assays can be used in which neutralizing antibodies capable of binding hSLAP-2 polypeptide specifically compete with a test compound for binding to hSLAP-2 polypeptide. In this manner, the antibodies can be used to detect the presence of any peptide which shares one or more antigenic determinants with the hSLAP-2 polypeptide.

Transgenics and Knock Outs

The present invention further encompasses transgenic non-human mammals, preferably mice, that comprise a recombinant expression vector harboring a nucleic acid sequence that encodes human hSLAP-2 comprising the amino acid sequence of SEQ ID NO:2.

Transgenic non-human mammals useful to produce recombinant proteins are well known to the skilled practitioner, as are the expression vectors necessary and the techniques for generating transgenic animals. Generally, the transgenic animal comprises a recombinant expression vector in which the nucleotide sequence that encodes human hSLAP-2 is operably linked to a tissue specific promoter whereby the coding sequence is only expressed in that specific tissue. For example, the tissue specific promoter can be a mammary cell specific promoter and the recombinant protein so expressed is recovered from the animal's milk.

The transgenic animals, particularly transgenic mice, containing a nucleic acid molecule which encodes human hSLAP-2 may be used as animal models for studying in vivo the overexpression of hSLAP-2 and for use in drug evaluation and discovery efforts to find compounds effective to inhibit or modulate the activity of hSLAP-2, such as, for example, compounds for treating immune system related conditions, diseases, or disorders, T-cell and B-cell neoplasms; inflammation disorders, diseases and conditions, rheumatoid arthritis, osteoarthritis, psoriasis, rhinitis, inflammatory bowel disease (Crohn's and ulcerative colitis), allergies, particularly those involving hyperactivity of B-cells and T-cells, or other immune cells, such as mast cells or eosinophils; autoimmune diseases such as systemic lupus erythematosus and multiple sclerosis; pulmonary diseases including asthma, acute respiratory distress syndrome, and chronic obstructive pulmonary disorder; tissue/organ rejection; and cancer. One having ordinary skill in the art using standard techniques, such as those taught in U.S. Pat. No. 4,873,191, issued Oct. 10, 1989 to Wagner et al. and in U.S. Pat. No. 4,736,866, issued Apr. 12, 1988 to Leder et al., can produce transgenic animals which produce the human hSLAP-2, or splice variants thereof, and use the animals in drug evaluation and discovery projects.

Another aspect of the present invention relates to knockout mice and methods of using the same. In particular, transgenic mice may be generated which are homozygous for a mutated, non-functional hSLAP-2 gene which is introduced into the animals using well-known techniques. The knockout mice produce no functional hSLAP-2 and thus are useful to study the function of hSLAP-2. Furthermore, the mice may be used in assays to study the effect of test compounds in hSLAP-2 deficient animals. For instance, hSLAP-2-deficient mice can be used to determine if, how and to what extent hSLAP-2 inhibitors will effect the animal and thus address concerns associated with inhibiting the activity of the molecule.

Methods of generating genetically deficient "knockout" mice are well known and are disclosed in M. R. Capecchi, 1989, *Science*, 244:1288-1292 and P. Li et al., 1995, *Cell*, 80:401-411. The human hSLAP-2 cDNA clone can be used to isolate a murine hSLAP-2 genomic clone. The genomic clone can be used to prepare a hSLAP-2 targeting construct which can disrupt the hSLAP-2 gene in the mouse by homologous recombination. The targeting construct contains a non-functioning portion of the hSLAP-2 gene which inserts in place of the functioning portion of the native mouse gene. The non-functioning insert generally contains an insertion in the exon that encodes the active region of hSLAP-2. The targeting construct can contain markers for both positive and negative selection. The positive selection marker allows for the selective elimination of cells which do not carry the marker, while the negative selection marker allows for the elimination of cells that carry the marker.

For example, a first selectable marker is a positive marker that will allow for the survival of cells carrying it. In some instances, the first selectable marker is an antibiotic resistance gene, such as the neomycin resistance gene, which can be placed within the coding sequence of the hSLAP-2 gene to render it non-functional, while at the same time rendering the construct selectable. The antibiotic resistance gene is within the homologous region which can recombine with native sequences. Thus, upon homologous recombination, the non-functional and antibiotic resistance selectable gene sequences will be taken up. Knockout mice may be used as models, in particular, the Cre-Lox model, for studying B- and T-cell related disorder and hyperactivity and screening compounds for treating these disorders.

The targeting construct also contains a second selectable marker which is a negative selectable marker. Cells with the negative selectable marker will be eliminated. The second selectable marker is outside the recombination region. Thus, if the entire construct is present in the cell, both markers will be present. If the construct has recombined with native sequences, the first selectable marker will be incorporated into the genome and the second will be lost. The herpes simplex virus thymidine kinase (HSV tk) gene is an example of a negative selectable marker which can be used as a second marker to eliminate cells that carry it. Cells with the HSV tk gene are selectively killed in the presence of gangcyclovir.

Cells are transfected with targeting constructs and then selected for the presence of the first selection marker and the absence of the second. Constructs/DNA are then injected into the blastocyst stage and implanted into pseudopregnant females. Chimeric offspring which are capable of transferring the recombinant genes in their germline are selected, mated and their offspring examined for heterozygous carriers of the recombined genes. Mating of the heterozygous offspring can then be used to generate fully homozygous offspring which constitute hSLAP-2-deficient knockout mice.

EXAMPLES

The Examples below are provided to illustrate the subject invention and are not intended to limit the invention.

Example 1

Methods

Cloning of the Full Length Human hSLAP-2 Gene

The LifeSeq EST database (Incyte Pharmaceuticals, Inc., California) was screened for novel SH2/SH3 domain genes using an SH2/SH3 domain hidden Markov model (HMM) from the Pfam database (A. Bateman et al., 2000, "The Pfam protein families database", *Nucleic Acids Res.*, 28:263-266) and the Genewise/Wise2 software package (Wise2 Documentation (version 2.1.20 stable), Ewan Birney, Richard Copley Sanger Centre, Wellcome Trust Genome Campus, Hinxton, Cambridge B10 1SA, England;

http://www.sanger.ac.uk/Software/Wise2/wisedocs/wise2/wise2.html). One novel SH2/SH3 domain-containing sequence was identified (clone 3182427). Sequencing and analysis of this clone indicated that it contained the full length coding region of a new gene.

To further elucidate the complete structure of this gene, full-length cloning experiments were performed using the GeneTrapper™ (LifeTechnologies, Inc.; Gaithersburg, Md.). Briefly, PCR primers PY749 (5'-CGGATCAGACACTA-CAGGATC-3'), (SEQ ID NO:3) and PY751 (5'-CGTCAT-TCAGGCTGATGTAG-3'), (SEQ ID NO:4) were used to screen the human leukocyte cDNA library. The GeneTrapper™ primer, PY750 (5'-TACTCTGAGCTGGCGGATGA-CATCTGCTGC-3'), (SEQ ID NO:5), used to screen a human leukocyte cDNA library (Life Technologies), identified positive clones containing the novel sequence. End-sequencing analysis revealed that one of the clones (clone #13) contained the full-length coding region of the new gene. The entire clone was subjected to sequence analysis with additional primers. The vector for this cDNA insert is pCMVSPORT2 with cloning sites SalI (5'-end) and NotI (3'-end). Sequence analyses were performed using the GCG/Wisconsin package (Genetics Computer Group, Madison, Wis.).

Sequence Analysis

As shown in FIGS. 1-3, sequencing of one of the isolated cDNA clones, clone #13, showed that this isolate has a 2567 nucleotide coding region, encoding a polypeptide of 261 amino acids. Sequence analysis revealed that the new gene has an SH3 domain (residues 35 to 90) and a SH2/SH3 domain (residues 94 to 176). Database searching against human genes showed that this novel protein exhibits the highest level of homology (~47% identity and ~58% similarity over 219 amino acids) with hSLAP (FIGS. 4-7). In addition, the new gene also shows significant homology to the SH2/SH3/SH3 regions of the Lyn and Hck tyrosine kinases from the Src-family (41% identity over 172 amino acids) which would be expected in this SLAP-family of proteins.

Example 2

Northern Analysis

Northern analysis is used to detect the presence of a transcript of a gene and involves the hybridization of a labeled nucleotide sequence to a membrane on which RNA from a particular cell or tissue type has been bound (see, J. Sambrook et al., supra). Electronic Northern analysis indicated that the novel gene of the present invention had a restricted expression profile, demonstrating detection of mRNAs in immune system tissues, embryonic structures, and the digestive tract (FIG. 8). Immune system cells included peripheral blood lymphocytes, Jurkat T-cells and bone-marrow cells. Embryonic structures included the placenta and the digestive tract included both the colon and the small intestine. The placenta may have been positive for expression due to the presence of immune system cells, and intestinal tissue may have been positive for expression due to the presence of intraepithelial lymphocytes (IELs). Analogous computer techniques using BLAST (S. F. Altschul, 1993, *J. Mol. Evol.*, 36:290-300 and S. F. Altschul et al., 1990, *J. Mol. Evol.*, 215:403-410) can be used to search for identical or related molecules in nucleotide databases, such as GenBank or the LIFESEQ database (Incyte Pharmaceuticals). This analysis is much more rapid and less labor-intensive than performing multiple, membrane-based hybridizations. In addition, the sensitivity of the computer search can be modified to determine whether any particular match is categorized as being exact (identical) or homologous.

The basis of the search is the product score, which is defined as follows: (% sequence identity×maximum BLAST score)/100. The product score takes into account both the degree of similarity between two sequences and the length of the sequence match. For example, with a product score of 40, the match will be exact within a 1-2% error; at 70, the match will be exact. Homologous molecules are usually identified by selecting those which show product scores between 15 and 40, although lower scores may identify related molecules. The results of Northern analysis are reported as a list of libraries in which the transcript encoding hSLAP-2 occurs. Abundance and percent abundance are also reported. Abundance directly reflects the number of times that a particular transcript is represented in a cDNA library, and percent abundance is abundance divided by the total number of sequences that are examined in the cDNA library.

Example 3

Labeling of Hybridization Probes and Use Thereof

Hybridization probes derived from SEQ ID NO:1 are employed to screen cDNAs, genomic DNAs, or mRNAs. Although the labeling of oligonucleotides containing about 20 base pairs is described in this Example, essentially the same procedure is used with larger cDNA fragments. Oligonucleotides are designed using state-of-the-art software such as OLIGO 4.06 (National Biosciences), labeled by combining 50 pmol of each oligomer and 250 µCi of [$\gamma$-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Amersham Pharmacia Biotech). A portion containing $10^7$ counts per minute of each of the sense and antisense oligonucleotides is used in a typical membrane based hybridization analysis of human genomic DNA digested with one of the following endonucleases (e.g., Ase I, Bgl II, Eco RI, Pst I, Xba 1, or Pvu II, DuPont NEN).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMATAR film (Kodak; Rochester, N.Y.) is exposed to the blots in a Phosphoimager cassette (Molecular Dynamics; Sunnyvale, Calif.) for several hours, hybridization patterns are compared visually.

Example 4

Complementary Polynucleotides

Anti-sense molecules or nucleic acid sequence complementary to the hSLAP-2 protein-encoding sequence, or any part thereof, is used to decrease or to inhibit the expression of naturally occurring hSLAP-2. Although the use of anti-sense or complementary oligonucleotides comprising about 15 to 35 base-pairs is described, essentially the same procedure is used with smaller or larger nucleic acid sequence fragments. An oligonucleotide based on the coding sequence of hSLAP-2 protein, as shown in FIGS. 2 and 3A-3B, is used to inhibit expression of naturally occurring hSLAP-2. The complementary oligonucleotide is designed from the most unique 5' sequence (FIGS. 1 and 3A-3B), and is used either to inhibit transcription by preventing promoter binding to the coding sequence, or to inhibit translation by preventing the ribosome from binding to the hSLAP-2 protein-encoding transcript. Using an appropriate portion of the signal and 5' sequence of SEQ ID NO:1, an effective anti-sense oligonucleotide includes any of about 15-35 nucleotides spanning the region which translates into the signal or 5' coding sequence of the polypeptide as shown in FIGS. 2 and 3A-3B. Appropriate oligonucleotides are designed using OLIGO 4.06 software and the hSLAP-2 protein coding sequence (SEQ ID NO:1).

Example 5

Microarrays

For the production of oligonucleotides for a microarray, SEQ ID NO:1 is examined using a computer algorithm which starts at the 3 prime end of the nucleotide sequence. The algorithm identifies oligomers of defined length that are unique to the gene, have a GC content within a range that is suitable for hybridization and lack predicted secondary structure that would interfere with hybridization. The algorithm identifies specific oligonucleotides of 20 nucleotides in length, i.e., 20-mers. A matched set of oligonucleotides is created in which one nucleotide in the center of each sequence is altered. This process is repeated for each gene in the microarray, and double sets of 20-mers are synthesized in the presence of fluorescent or radioactive nucleotides and arranged on the surface of a substrate. When the substrate is a silicon chip, a light-directed chemical process is used for deposition (WO 95/11995, M. Chee et al.).

Alternatively, a chemical coupling procedure and an ink jet device is used to synthesize oligomers on the surface of a substrate. (WO 95/25116, J. D. Baldeschweiler et al.). As another alternative, a "gridded" array that is analogous to a dot (or slot) blot is used to arrange and link cDNA fragments or oligonucleotides to the surface of a substrate using, for example, a vacuum system, or thermal, UV, mechanical, or chemical bonding techniques. A typical array may be produced by hand, or by using available materials and equipment, and may contain grids of 8 dots, 24 dots, 96 dots, 384 dots, 1536 dots, or 6144 dots. After hybridization, the microarray is washed to remove any non-hybridized probe, and a detection device is used to determine the levels and patterns of radioactivity or fluorescence. The detection device may be as simple as X-ray film, or as complicated as a light scanning apparatus. Scanned fluorescent images are examined to determine degree of complementarity and the relative abundance/expression level of each oligonucleotide sequence in the microarray.

Example 6

Purification of Naturally Occurring HSLAP-2 Protein Using Specific Antibodies

Naturally occurring or recombinant hSLAP-2 polypeptide is substantially purified by immunoaffinity chromatography using antibodies specific for the hSLAP-2 polypeptide, or a peptide derived therefrom. An immunoaffinity column is constructed by covalently coupling polypeptide antibody raised against hSLAP-2 to an activated chromatographic resin, such as CNBr-activated SEPHAROSE (Amersham Pharmacia Biotech, Inc.; Piscataway, N.J.). After the coupling, the resin is blocked and washed according to the manufacturer's instructions.

Medium containing hSLAP-2 polypeptide is passed over the immunoaffinity column, and the column is washed under conditions that allow the preferential absorbance of the hSLAP-2 polypeptide (e.g., high ionic strength buffers in the presence of detergent). The column is eluted under conditions that disrupt antibody/hSLAP-2 polypeptide binding (e.g., a buffer of pH 2-3, or a high concentration of a chaotrope, such as urea or thiocyanate ion), and hSLAP-2 polypeptide is collected.

Example 7

Identification of Molecules that Interact with the Human SLAP-2 Protein hSLAP-2 polypeptide, or biologically active fragments thereof, are labeled with $^{125}$I Bolton-Hunter reagent (Bolton et al., 1973, *Biochem. J,* 133:529). Candidate molecules previously arrayed in wells of a multi-welled plate are incubated with the labeled hSLAP-2 polypeptide, washed, and any wells having labeled hSLAP-2 polypeptide-candidate molecule complexes are assayed. Data obtained using different concentrations of the hSLAP-2 polypeptide are used to calculate values for the number, affinity and association of the hSLAP-2 polypeptide with the candidate molecules. In addition, data may be obtained using fusion proteins such as GST- or polyhistidine tagged fusion proteins, co-immunoprecipitation and/or Western immunoblotting, etc.

The contents of all patents, patent applications, published PCT applications and articles, books, references, reference manuals and abstracts cited herein are hereby incorporated by reference in their entirety to more fully describe the state of the art to which the invention pertains.

As various changes can be made in the above-described subject matter without departing from the scope and spirit of the present invention, it is intended that all subject matter contained in the above description, or defined in the appended claims, be interpreted as descriptive and illustrative of the present invention. Many modifications and variations of the present invention are possible in light of the above teachings.

What is claimed is:

1. An isolated polypeptide comprising a polypeptide sequence selected from the group consisting of:
   (a) an isolated polypeptide comprising amino acids 1 to 261 of SEQ ID NO:2;
   (b) an isolated polypeptide comprising amino acids 2 to 261 of SEQ ID NO:2;
   (c) an isolated polypeptide comprising a polypeptide sequence encoded by nucleotides 415 to 1197 of SEQ ID NO:1; and
   (d) an isolated polypeptide comprising a polypeptide sequence encoded by nucleotides 418 to 1197 of SEQ ID NO:1.

2. The isolated polypeptide of claim 1, wherein said polypeptide is (a).

3. The isolated polypeptide of claim 1, wherein said polypeptide is (b).

4. The isolated polypeptide of claim 1, wherein said polypeptide is (c).

5. The isolated polypeptide of claim 1, wherein said polypeptide is (d).

6. An isolated polypeptide produced by a method comprising:
   (a) culturing an isolated recombinant host cell comprising a vector that comprises the coding region encoding the polypeptide of claim 1 under conditions such that the polypeptide of claim 1 is expressed; and
   (b) recovering said polypeptide.

7. An isolated polypeptide comprising the polypeptide encoded by the hSLAP-2 cDNA clone contained in ATCC Deposit No: PTA-3873.

8. An isolated polypeptide consisting of amino acids from position 35 to position 90 of SEQ ID NO:2.

9. An isolated polypeptide consisting of amino acids from position 94 to position 176 of SEQ ID NO:2.

* * * * *

SEQUENCE LISTING

<160> NUMBER OF SEQ ID NOS: 7

<210> SEQ ID NO 1
<211> LENGTH: 2567
<212> TYPE: DNA
<213> ORGANISM: Homo sapiens

<400> SEQUENCE: 1

| | | | | | |
|---|---|---|---|---|---|
| cccacgcgtc | cggtcggagc | tagagctcca | aggaccccac | gcctgtgtct | ctgtgacaga | 60 |
| gctcaaaggg | ccctgggcct | tccctccctg | gctcggctgt | gcttgggagg | gttccccagt | 120 |
| ccagaatccc | taaggagcat | ggggcagctg | atccatccct | ggtgtacaaa | ctgctgactg | 180 |
| cagacagatg | ctgagctacc | caaaccaaca | cctagcctct | ccctgaagat | cctcccaggc | 240 |
| tgagagagtt | ctgggtgtcc | taggaccaag | gacactggca | gacttccaga | agggccccca | 300 |
| aagccctaac | ctgtccagcc | agagcatgcg | tctcagcaga | gctgtcttcc | caagcctttg | 360 |
| atgacaaacc | aatttccctc | gatgatgtgc | ttctgagtgc | tctgctgagg | aacaatggga | 420 |
| agtctgccca | gcagaagaaa | atctctgcca | agcccaagct | tgagttcctc | tgtccaaggc | 480 |
| cagggacctg | tgaccatgga | agcagagaga | agcaaggcca | cagccgtggc | cctgggcagt | 540 |
| ttcccggcag | gtgccccggc | cgagctgtcg | ctgagactcg | gggagccatt | gaccatcgtc | 600 |
| tctgaggatg | gagactggtg | gacggtgctg | tctgaagtct | caggcagaga | gtataacatc | 660 |
| cccagcgtcc | acgtggccaa | agtctcccat | gggtggctgt | atgagggcct | gagcagggag | 720 |
| aaagcagagg | aactgctgtt | gttacctggg | aaccctggag | gggccttcct | catccgggag | 780 |
| agccagacca | ggagaggctc | ttactctctg | tcagtccgcc | tcagccgccc | tgcatcctgg | 840 |
| gaccggatca | gacactacag | gatccactgc | cttgacaatg | gctggctgta | catctcaccg | 900 |
| cgcctcacct | tccctcact | ccaggccctg | gtgaccatt | actctgagct | ggcggatgac | 960 |
| atctgctgcc | tactcaagga | gccctgtgtc | ctgcagaggg | ctggcccgct | ccctggcaag | 1020 |
| gatataccc | tacctgtgac | tgtgcagagg | acaccactca | actggaaaga | gctgacagc | 1080 |
| tccctcctgt | tttctgaagc | tgccacaggg | gaggagtctc | ttctcagtga | gggtctccgg | 1140 |
| gagtccctca | gcttctacat | cagcctgaat | gacgaggctg | tctctttgga | tgatgcctag | 1200 |
| gcccaaagga | gaggccaaaa | gggaaaccaa | ggctgcacac | ctagaacccc | aattcagcct | 1260 |
| cctgggcacc | ccagaggcaa | ggctgtgcac | tcagggaggg | aggtgggac | acagaggtgc | 1320 |
| atctagggtc | ccacctgtac | ccttgctctt | tcctctctta | gcccttagaa | gtcacctact | 1380 |
| tccttccagt | gccatgatcc | cacctgcgac | ctctagtgcg | agtgcagaga | aggtgggacc | 1440 |
| agggccaggg | ttccaaaaag | agaataagcc | tcctgggggg | tctgacctag | ttagttcttg | 1500 |
| agtttgggt | ttccagtacc | atctggatgc | cctgcctgtt | gagccccatt | ctacatcccc | 1560 |
| accattaacc | aggccccacc | cacaaggtag | aaacaacccc | tagagtcaac | gagaaagtca | 1620 |
| ttttcagaaa | atctacaagt | ctcgttgaga | ccaccaccat | acctcagaag | gtaggactgt | 1680 |
| ggcctagaag | ggaaaggaaa | gctgagatga | tgtcttaccg | tagcagcaga | tcttggatgg | 1740 |
| tccaggctct | atgtgacctc | cagagcaaag | agaaagactt | cggacagtct | aggtcctcaa | 1800 |
| atgtcccca | ttgaggacaa | cagccccagc | tctttttctt | tttttttgag | acggagtctt | 1860 |
| gccctgttgc | ccatgctgga | gtgcaatggc | acgatctcag | ctcactgcaa | cctccatctc | 1920 |
| ctggattcaa | acaattctcc | tgcctcagcc | tccagaatag | ctgggattac | aggcgtacac | 1980 |
| caccatgcct | ggctaatttt | tttgtatttt | tagtagacat | ggggtttcac | cacattggcc | 2040 |

-continued

```
aggctggtgt cgaactcctg acctcaggtg atccacccac cttggcctcc caaagtgctg    2100
ggattacagg tgtgagccac ggcacccagc ctagctctca gatctctatt tcattttgtg    2160
gcttaccatt ccctagcaca ctggccttgc catcttgtgg ccgaataaaa aataacacct    2220
cttaagtcta gcacactgca gtgaggccag gcacctcagt gctgggcagg ggcatcagaa    2280
ggtgctaagc cctctctcca caatgccaag acggagacca cagcctacac caaatccagc    2340
ccttgatttc cctgctgcct ccataaacag aaagaggtct gctggatccg ctaagggatc    2400
agggagagga agaaagaggg atggggtggg aggcacccccc tccagtgctc ctactggttc    2460
ccaagctaca ggtggggtgg gaaaggcttt atcaggtatc atcaacaggt tctcaattaa    2520
agatttgatt tattcaagta tgtgaaaaaa aaaaaaaaaa aaaaaaa                  2567
```

<210> SEQ ID NO 2
<211> LENGTH: 261
<212> TYPE: PRT
<213> ORGANISM: Homo sapiens

<400> SEQUENCE: 2

```
Met Gly Ser Leu Pro Ser Arg Arg Lys Ser Leu Pro Ser Pro Ser Leu
  1               5                  10                  15

Ser Ser Ser Val Gln Gly Gln Gly Pro Val Thr Met Glu Ala Glu Arg
             20                  25                  30

Ser Lys Ala Thr Ala Val Ala Leu Gly Ser Phe Pro Ala Gly Gly Pro
         35                  40                  45

Ala Glu Leu Ser Leu Arg Leu Gly Glu Pro Leu Thr Ile Val Ser Glu
     50                  55                  60

Asp Gly Asp Trp Trp Thr Val Leu Ser Glu Val Ser Gly Arg Glu Tyr
 65                  70                  75                  80

Asn Ile Pro Ser Val His Val Ala Lys Val Ser His Gly Trp Leu Tyr
                 85                  90                  95

Glu Gly Leu Ser Arg Glu Lys Ala Glu Glu Leu Leu Leu Leu Pro Gly
            100                 105                 110

Asn Pro Gly Gly Ala Phe Leu Ile Arg Glu Ser Gln Thr Arg Arg Gly
        115                 120                 125

Ser Tyr Ser Leu Ser Val Arg Leu Ser Arg Pro Ala Ser Trp Asp Arg
    130                 135                 140

Ile Arg His Tyr Arg Ile His Cys Leu Asp Asn Gly Trp Leu Tyr Ile
145                 150                 155                 160

Ser Pro Arg Leu Thr Phe Pro Ser Leu Gln Ala Leu Val Asp His Tyr
                165                 170                 175

Ser Glu Leu Ala Asp Asp Ile Cys Cys Leu Leu Lys Glu Pro Cys Val
            180                 185                 190

Leu Gln Arg Ala Gly Pro Leu Pro Gly Lys Asp Ile Pro Leu Pro Val
        195                 200                 205

Thr Val Gln Arg Thr Pro Leu Asn Trp Lys Glu Leu Asp Ser Ser Leu
    210                 215                 220

Leu Phe Ser Glu Ala Ala Thr Gly Glu Glu Ser Leu Leu Ser Glu Gly
225                 230                 235                 240

Leu Arg Glu Ser Leu Ser Phe Tyr Ile Ser Leu Asn Asp Glu Ala Val
                245                 250                 255

Ser Leu Asp Asp Ala
            260
```

```
<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: PY749 PCR
      PRIMER

<400> SEQUENCE: 3
cggatcagac actacaggat c                                              21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: PY751 PCR
      PRIMER

<400> SEQUENCE: 4
cgtcattcag gctgatgtag                                                20

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: GENE
      TRAPPER PY750 PRIMER

<400> SEQUENCE: 5
tactctgagc tggcggatga catctgctgc                                     30

<210> SEQ ID NO 6
<211> LENGTH: 276
<212> TYPE: PRT
<213> ORGANISM: Homo sapiens

<400> SEQUENCE: 6
```

Met Gly Asn Ser Met Lys Ser Thr Pro Ala Pro Ala Glu Arg Pro Leu
1               5                   10                  15

Pro Asn Pro Glu Gly Leu Asp Ser Asp Phe Leu Ala Val Leu Ser Asp
            20                  25                  30

Tyr Pro Ser Pro Asp Ile Ser Pro Ile Phe Arg Arg Gly Glu Lys
        35                  40                  45

Leu Arg Val Ile Ser Asp Glu Gly Gly Trp Trp Lys Ala Ile Ser Leu
    50                  55                  60

Ser Thr Gly Arg Glu Ser Tyr Ile Pro Gly Ile Cys Val Ala Arg Val
65                  70                  75                  80

Tyr His Gly Trp Leu Phe Glu Gly Leu Gly Arg Asp Lys Ala Glu Glu
                85                  90                  95

Leu Leu Gln Leu Pro Asp Thr Lys Val Gly Ser Phe Met Ile Arg Glu
            100                 105                 110

Ser Glu Thr Lys Lys Gly Phe Tyr Ser Leu Ser Val Arg His Arg Gln
        115                 120                 125

Val Lys His Tyr Arg Ile Phe Arg Leu Pro Asn Asn Trp Tyr Tyr Ile
    130                 135                 140

Ser Pro Arg Leu Thr Phe Gln Cys Leu Glu Asp Leu Val Asn His Tyr
145                 150                 155                 160

Ser Glu Val Ala Asp Gly Leu Cys Cys Val Leu Thr Thr Pro Cys Leu
                165                 170                 175

```
Thr Gln Ser Thr Ala Ala Pro Ala Val Arg Ala Ser Ser Ser Pro Val
            180                 185                 190

Thr Leu Arg Gln Lys Thr Val Asp Trp Arg Arg Val Ser Arg Leu Gln
            195                 200                 205

Glu Asp Pro Glu Gly Thr Glu Asn Pro Leu Gly Val Asp Glu Ser Leu
    210                 215                 220

Phe Ser Tyr Gly Leu Arg Glu Ser Ile Ala Ser Tyr Leu Ser Leu Thr
225                 230                 235                 240

Ser Glu Asp Asn Thr Ser Phe Asp Arg Lys Lys Ser Ile Ser Leu
                245                 250                 255

Met Tyr Gly Gly Ser Lys Arg Lys Ser Ser Phe Ser Ser Pro Pro
            260                 265                 270

Tyr Phe Glu Asp
        275

<210> SEQ ID NO 7
<211> LENGTH: 281
<212> TYPE: PRT
<213> ORGANISM: Mus musculus

<400> SEQUENCE: 7

Met Gly Asn Ser Met Lys Ser Thr Ser Pro Ser Glu Arg Pro Leu
 1               5                  10                  15

Ser Ser Ser Glu Gly Leu Glu Ser Asp Phe Leu Ala Val Leu Thr Asp
            20                  25                  30

Tyr Pro Ser Pro Asp Ile Ser Pro Ile Phe Arg Arg Gly Glu Lys
        35                  40                  45

Leu Arg Val Ile Ser Asp Gly Gly Trp Trp Lys Ala Ile Ser Leu
    50                  55                  60

Ser Thr Gly Arg Glu Ser Tyr Ile Pro Gly Ile Cys Val Ala Arg Val
 65                 70                  75                  80

Tyr His Gly Trp Leu Phe Glu Gly Leu Gly Arg Asp Lys Ala Glu Glu
                85                  90                  95

Leu Leu Gln Leu Pro Asp Thr Lys Ile Gly Ser Phe Met Ile Arg Glu
            100                 105                 110

Ser Glu Thr Lys Lys Gly Phe Tyr Ser Leu Ser Val Arg His Arg Gln
            115                 120                 125

Val Lys His Tyr Arg Ile Phe Arg Leu Pro Asn Asn Trp Tyr Tyr Ile
            130                 135                 140

Ser Pro Arg Leu Thr Phe Gln Cys Leu Glu Asp Leu Val Thr His Tyr
145                 150                 155                 160

Ser Glu Val Ala Asp Gly Leu Cys Cys Val Leu Thr Thr Pro Cys Leu
                165                 170                 175

Ala Gln Asn Ile Pro Ala Pro Thr Ser His Pro Ser Pro Cys Thr Ser
            180                 185                 190

Pro Gly Ser Pro Val Thr Leu Arg Gln Lys Thr Phe Asp Trp Lys Arg
        195                 200                 205

Val Ser Arg Leu Gln Glu Gly Ser Glu Gly Ala Glu Asn Pro Leu Arg
    210                 215                 220

Val Asp Glu Ser Leu Phe Ser Tyr Gly Leu Arg Glu Ser Ile Ala Ser
225                 230                 235                 240

Tyr Leu Ser Leu Thr Gly Asp Asp Ser Ser Ser Phe Asp Arg Lys Lys
                245                 250                 255
```

```
Lys Ser Leu Ser Leu Met Tyr Thr Gly Ser Lys Arg Lys Ser Ser Phe
            260                 265                 270

Phe Ser Ala Pro Gln Tyr Phe Glu Asp
            275                 280
```